(12) United States Patent
Moriuchi et al.

(10) Patent No.: US 11,656,182 B2
(45) Date of Patent: May 23, 2023

(54) METHOD, COMPOSITION, AND CHIP FOR DETECTING ANALYTE IN BLOOD SAMPLE

(71) Applicant: TERUMO KABUSHIKI KAISHA, Tokyo (JP)

(72) Inventors: Takeyuki Moriuchi, Nakakoma-gun (JP); Yusuke Komata, Katsushika-ku (JP); Fumihiko Chai, Nakakoma-gun (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 57 days.

(21) Appl. No.: 17/335,409

(22) Filed: Jun. 1, 2021

(65) Prior Publication Data

US 2021/0293722 A1 Sep. 23, 2021

Related U.S. Application Data

(60) Division of application No. 16/275,233, filed on Feb. 13, 2019, now Pat. No. 11,150,193, which is a continuation of application No. PCT/JP2017/028488, filed on Aug. 4, 2017.

(30) Foreign Application Priority Data

Sep. 28, 2016 (JP) .............................. JP2016-190379

(51) Int. Cl.
  *G01N 21/78* (2006.01)
  *G01N 33/66* (2006.01)
  *G01N 33/92* (2006.01)
  *G01N 33/50* (2006.01)

(52) U.S. Cl.
  CPC ............. *G01N 21/78* (2013.01); *G01N 33/50* (2013.01); *G01N 33/66* (2013.01); *G01N 33/92* (2013.01)

(58) Field of Classification Search
  CPC .......... C12Q 1/26; G01N 21/77; G01N 21/78; G01N 33/48; G01N 33/50; G01N 33/52; G01N 33/66; G01N 33/92; Y10T 436/145555; Y10T 436/147777; Y10T 436/17
  USPC ......... 436/63, 71, 95, 96, 98, 106, 164, 166; 422/400, 401, 82.05, 82.09
  See application file for complete search history.

(56) References Cited

U.S. PATENT DOCUMENTS

| | | | |
|---|---|---|---|
| 3,740,143 A | 6/1973 | Groner et al. |
| 4,279,506 A | 7/1981 | Maines |
| 4,290,772 A | 9/1981 | Frey |
| 4,577,964 A | 3/1986 | Hansen, Jr. |

(Continued)

FOREIGN PATENT DOCUMENTS

| | | |
|---|---|---|
| CN | 103674870 A | 3/2014 |
| EP | 1 329 722 A1 | 7/2003 |

(Continued)

OTHER PUBLICATIONS

International Searching Authority, "International Search Report," issued in connection with International Patent Application No. PCT/JP2017/028488, dated Nov. 28, 2017.

(Continued)

*Primary Examiner* — Maureen Wallenhorst
(74) *Attorney, Agent, or Firm* — Foley & Lardner LLP

(57) ABSTRACT

A composition for detecting an analyte in a blood sample includes: a coloring reagent; an oxidoreductase; and a refractive index adjuster.

8 Claims, 9 Drawing Sheets

(56) References Cited

U.S. PATENT DOCUMENTS

| | | | |
|---|---|---|---|
| 4,734,360 A | | 3/1988 | Phillips |
| 10,648,015 B2* | | 5/2020 | Sato ..................... G01N 21/272 |
| 11,130,982 B2* | | 9/2021 | Sato ......................... C12Q 1/54 |
| 11,150,193 B2* | | 10/2021 | Moriuchi ................ G01N 21/78 |
| 2004/0063213 A1 | | 4/2004 | Hirai et al. |
| 2006/0135870 A1 | | 6/2006 | Webler |
| 2007/0105230 A1 | | 5/2007 | Perez et al. |
| 2007/0154975 A1* | | 7/2007 | Watzele ................. G01N 21/78 435/23 |
| 2020/0371020 A1 | | 11/2020 | Chai et al. |

FOREIGN PATENT DOCUMENTS

| | | |
|---|---|---|
| EP | 1 621 887 A1 | 2/2006 |
| JP | 55-063760 A | 5/1980 |
| JP | 63-210664 A | 9/1988 |
| JP | 2006-087356 A | 4/2006 |
| JP | 2007-114026 A | 5/2007 |
| JP | 2008-148656 A | 7/2008 |
| JP | 2009-515194 A | 4/2009 |
| JP | 2016-038230 A | 3/2016 |
| JP | 2016-151417 A | 8/2016 |
| WO | WO-2003-005039 A1 | 10/2004 |
| WO | WO-2016-147527 A1 | 9/2016 |

OTHER PUBLICATIONS

International Searching Authority, "Written Opinion," issued in connection with International Patent Application No. PCT/JP2017/028488, dated Nov. 28, 2017.

Extended European Search Report dated April 17, 2020 for corresponding European Patent Application No. 17855442.4.

Brezinski et al., "Index Matching to Improve Optical Coherence Tomography Imaging Through Blood," Circulation, Apr. 17, 2001, pp. 1999-2003.

Office Action dated May 18, 2021 issued in a corresponding Chinese Patent Application No. 201780045096.5, (22 pages).

* cited by examiner

METHOD, COMPOSITION, AND CHIP FOR DETECTING ANALYTE IN BLOOD SAMPLE

CROSS-REFERENCE TO RELATED APPLICATIONS

This application is a divisional of U.S. patent application Ser. No. 16/275,233, filed on Feb. 13, 2019 (now U.S. Pat. No. 11,150,193), which is a bypass continuation of PCT Application No. PCT/JP2017/028488 filed on Aug. 4, 2017, which claims priority to Japanese Application No. 2016-190379, filed on Sep. 28, 2016. The contents of these applications are hereby incorporated by reference in their entireties.

BACKGROUND

The present disclosure relates to a method, a composition, and a chip, which are used for detecting an analyte such as glucose contained in a blood sample.

BACKGROUND ART

In the related art, a technology of measuring an analyte (for example, glucose) contained in a blood sample by an electrochemical means (electrode method) or an optical means (colorimetric method) is known.

For example, JP 2008-148656 A describes a dry analytical element for measuring glucose or the like in blood, the dry analytical element including an anisotropic membrane having a larger size of pores on a surface at the side on which a sample is deposited than a size of pores at the side at which coloring is detected.

SUMMARY

In the disclosure described in JP 2008-148656 A, an anisotropic membrane having a large diameter of pores on a surface at the side on which a sample is deposited and a small size of pores on a surface at the side at which coloring is detected is used. According to this, a component having a large size such as a red blood cell among components derived from blood is filtrated without reaching the side at which coloring of the anisotropic membrane is detected. For this reason, in the disclosure described in JP 2008-148656 A, the chromogenic reaction is performed in the absence of the component having a large size such as a red blood cell. However, in the case of using such an anisotropic membrane, the pores may be clogged by components derived from the sample, foreign substances and the like, and this may affect measurement accuracy. Further, in a technique in which fractionation of such components derived from the blood sample is necessary, this technique may not be sufficient from the viewpoint of speediness of measurement.

On the other hand, it is known that, when analyte is measured by an optical means without fractionation of components derived from the blood sample, a base line becomes higher (that is, noise become stronger), so that it is difficult to perform measurement with high accuracy.

The embodiments described in the present disclosure have been developed in view of the above-described circumstances, and an object thereof is to provide a means capable of detecting an analyte with high accuracy without fractionation of a component derived from a blood sample.

The present inventors have conducted intensive studies in order to solve the above-described problems. As a result, the present inventors have found that the above-described issues can be solved by providing, to detection for an analyte, an analysis sample in which a difference in refractive index between a red blood cell and an extra-red blood cell fluid is reduced using a refractive index adjuster, as described in the present disclosure.

A first aspect of the present disclosure relates to a method for detecting an analyte in a blood sample, the method including:

(1) preparing the blood sample;
(2) obtaining an analysis sample in which a difference in refractive index between a red blood cell and an extra-red blood cell fluid is reduced by dissolving a refractive index adjuster in the blood sample; and
(3) detecting the analyte using the analysis sample.

A second aspect of the present disclosure relates to a composition for detecting an analyte in a blood sample, the composition containing a coloring reagent, an oxidoreductase, and a refractive index adjuster.

A third aspect of the present disclosure relates to a chip for detecting an analyte in a blood sample, the chip including: a reaction portion containing a coloring reagent, an oxidoreductase, and a refractive index adjuster.

DETAILED DESCRIPTION

Figure 1:
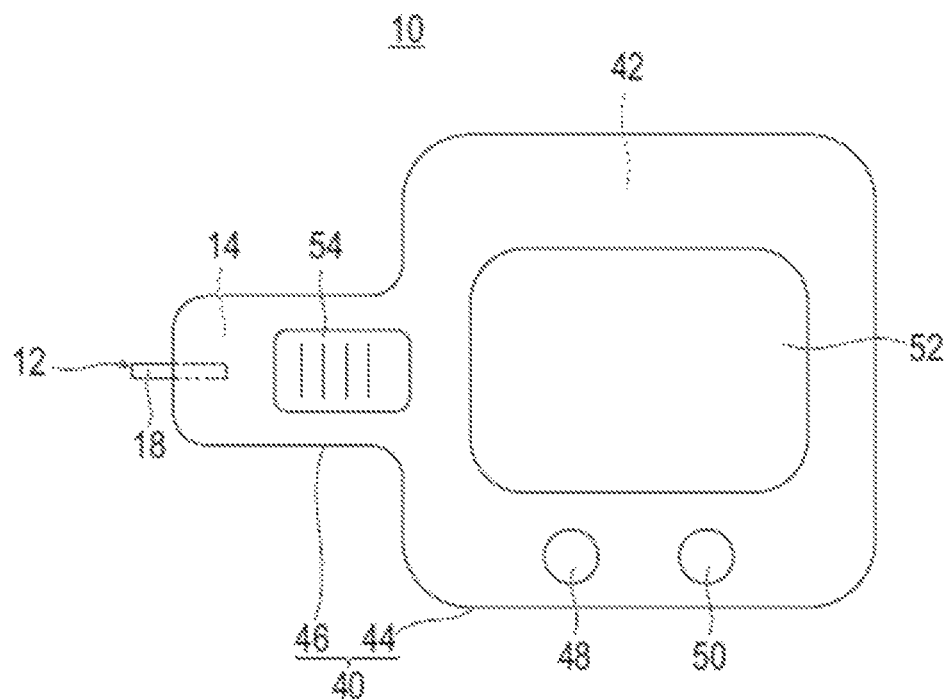
FIG. 1 is a plan view schematically illustrating a detection apparatus (component measurement apparatus) attached with a detection chip according to an embodiment.

A first aspect of the present disclosure relates to a method for detecting an analyte in a blood sample, the method including:

(1) preparing the blood sample;
(2) obtaining an analysis sample in which a difference in refractive index between a red blood cell and an extra-red blood cell fluid is reduced by dissolving a refractive index adjuster in the blood sample: and (3) detecting the analyte using the analysis sample.

A second aspect of the present disclosure relates to a composition for detecting an analyte in a blood sample, the composition containing a coloring reagent, an oxidoreductase, and a refractive index adjuster.

A third aspect of the present disclosure relates to a chip for detecting an analyte in a blood sample, the chip having a reaction portion containing coloring reagent, oxidoreductase, and refractive index adjuster.

In this application, a description of an aspect of the present disclosure may be appropriately modified and applied to other aspects mutually.

According to the present disclosure, an analyte can be detected with high accuracy without fractionation of a blood component. The present inventors have studied various factors of increasing the base line in a case in which the measurement of the analyte is performed by the optical means without fractionation of a component derived from a blood sample. The present inventors have found that, when the measurement of the analyte is performed by the optical means without fractionation of a component derived from a blood sample, light is scattered due to a difference in refractive index between a red blood cell and an extra-red blood cell fluid (that is, a component other than the red blood cell present in the sample), the base line derived from the scattering light becomes higher, and thus the measurement accuracy is degraded. With respect to such a problem, the present inventors have further found that, by dissolving a compound, which reduces the difference in refractive index between the red blood cell and the extra-red blood cell fluid, in the extra-red blood cell fluid, the measurement accuracy of the analyte is improved. For example, it is considered that, by performing the measurement of the analyte after dissolving a compound, which has a high osmotic pressure and also has a high refractive index when the compound is dissolved in the blood (for example, Acid Yellow 23 or the like in Embodiments), in the blood sample, the balance between the refractive index of the red blood cell itself, which is increased by contraction by the osmotic pressure, and the refractive index of the extra-red blood cell fluid is acquired, and according to this, scattering of light is suppressed. On the other hand, it is considered that, even in the case of a compound that has an osmotic pressure close to that of the red blood cell and in which the refractive index when the compound is dissolved in the blood is not as high as the above-described compound (for example, sucralose or the like in Embodiments), by performing the measurement of the analyte after dissolving the compound in the blood sample, the difference in refractive index of red blood cell/extra-red blood cell fluid is decreased by setting the refractive index of the extra-red blood cell fluid to be close to the refractive index of the inside of the blood cell while contraction of the red blood cell caused by the osmotic pressure is suppressed. Incidentally, the above-described mechanism is presumption and does not limit the technical scope of the present disclosure.

Hereinafter, an embodiment of the present disclosure will be described. Incidentally, the present disclosure is not limited only to the following embodiment. Further, for the convenience of description, the dimensional ratios of the drawings are exaggerated and may be different from the actual ratios.

In this application, "X to Y" indicating a range means "X or more and Y or less." Further, unless specified otherwise, operations and measurement of physical properties and the like are conducted under the conditions of room temperature (20 to 25° C.)/relative humidity of 40 to 50% RH.

<Method for Detecting Analyte in Blood Sample>

An aspect of the present disclosure relates to a method for detecting an analyte in a blood sample, the method including:

(1) preparing the blood sample;

(2) obtaining an analysis sample in which a difference in refractive index between a red blood cell and an extra-red blood cell fluid is reduced by dissolving a refractive index adjuster in the blood sample; and (3) detecting the analyte using the analysis sample.

In the method according to the aspect of the present disclosure, a blood sample is blood including red blood cells. According to the method of the aspect of the present disclosure, even in the case of using such a sample including a red blood cell, the analyte can be detected with high accuracy without fractionation of a blood component.

The blood sample may be a blood sample derived from humans or non-human animals. Examples of the non-human animals include laboratory animals such as mice, rats, and hamsters; pets such as dogs, cats, and rabbits; and livestock or domestic poultry such as pigs, cows, goats, sheep, horses, and chickens, but the non-human animals are not limited thereto. Preferably, the blood sample is derived from humans. Preferably, the blood sample is whole blood.

The "refractive index adjuster" in this application is adapted to reduce a difference in refractive index between red blood cell and an extra-red blood cell fluid by dissolving the refractive index adjuster in the blood. In the present application, the term "extra-red blood cell fluid" is defined as a fluid containing a blood sample-derived component other than the red blood cell, the refractive index adjuster, and other reagents that can be used, such as a coloring reagent.

The reduction of the difference in refractive index between the red blood cell and the extra-red blood cell fluid can be confirmed using, as an index, the fact that the transmittance of the analysis sample in a long wavelength range (for example, 700 nm to 950 nm) is higher than that of the blood sample. In a certain embodiment, the refractive index adjuster is dissolved in the blood sample such that the analysis sample has a wavelength with a transmittance of 50% or more within a range of 700 nm to 950 nm. That is, in the embodiment, there is provided a method for detecting an analyte in a blood sample, the method including:

(1) preparing the blood sample;

(2) preparing an analysis sample, which has a wavelength with a transmittance of 50% or more within a range of 700 nm to 950 nm, by dissolving a refractive index adjuster in the blood sample; and (3) detecting the analyte using the analysis sample.

In a preferred embodiment, the blood sample after the refractive index adjuster is dissolved (that is, the analysis sample) has a wavelength with a transmittance of 60% or more within a range of 700 nm to 950 nm, and more preferably has a wavelength with a transmittance of 65% or more within a range of 700 nm to 950 nm, and yet more preferably has a wavelength with a transmittance of 70% or more within a range of 700 nm to 950 nm.

In this application, the "transmittance" and the "absorbance" of the blood sample or the analysis sample are values measured at an optical path length of 50 μm, and can be obtained, for example, by the method described in the <Spectrum Analysis>section below. As a specific example of the measurement method of a transmittance (T (%)) described above, the transmittance can be obtained by calculation using a detection chip described in Embodiments from an absorbance (Abs) after 5 seconds and before 30 seconds after blood having a hematocrit value of 40 is deposited, according to the following formula. In a certain embodiment, the absorbance (Abs) of the following formula corresponds to an absorbance (Abs) at 810 nm.

$$\text{Transmittance (\%)} = \frac{100}{10^{abs}}$$

Incidentally, the method according to the aspect of the present disclosure is not limited to the method using the detection chip described below. For example, in a case in which analysis is performed using a cell having an optical path length of 10 mm, the "transmittance (%)" may be obtained from an absorbance that is obtained by correction in consideration of a concentration of an analyte in a blood sample present in a measurement cell, according to the Lambert-Beer law.

In an embodiment, the blood sample (that is, the analysis sample) after the refractive index adjuster is dissolved therein has a transmittance of 50% or more in a wavelength range of 800 nm to 950 nm, and the transmittance is more preferably 60% or more in a wavelength range of 800 nm to 900 nm, further preferably more than 65% in a wavelength range of 750 nm to 900 nm, even more preferably 70% or more in a wavelength range of 800 nm to 900 nm, and particularly preferably 70% or more in a wavelength range of 750 nm to 900 nm.

In an embodiment, the transmittance of the analysis sample is higher than the transmittance of the blood sample in a wavelength range of 750 nm to 850 nm. In another more preferred embodiment, the transmittance of the analysis sample is higher than the transmittance of the blood sample in a wavelength range of 650 nm to 900 nm. In another further preferred embodiment, the transmittance of the analysis sample is higher than the transmittance of the blood sample in a wavelength range of 600 nm to 950 nm.

In an embodiment, as the refractive index adjuster, a refractive index adjuster having a high transmittance at the absorption peak wavelength of the coloring reagent described below is employed. That is, in a case in which the detection of an analyte is performed using the coloring reagent, the molar absorbance coefficient of the refractive index adjuster at the absorption peak wavelength of the coloring reagent is preferably 200 L/(mol·cm) or less. By using such a refractive index adjuster in combination with the coloring reagent, the analyte can be detected with higher accuracy. The molar absorbance coefficient of the refractive index adjuster at the absorption peak wavelength of the coloring reagent is more preferably 150 L/(mol·cm) or less and further preferably 70 L/(mol·cm) or less (the lower limit is 0 L/(mol·cm)).

The wavelengths of 545 nm and 575 nm are peak wavelengths for absorption of hemoglobin. Therefore, by using an analysis sample having a high transmittance at those wavelengths, the amount of hemoglobin in an analysis sample based on the absorbance at a wavelength of 545 nm and/or 575 nm is easily calculated. Thus, by using an analysis sample having a high transmittance at wavelengths of 545 nm and 575 nm, there is an advantage that the content of the analyte is easily corrected on the basis of the amount of hemoglobin. That is, as for the analysis sample, it is preferable that a peak protruding downwardly is observed at least one wavelength of 545 nm and 575 nm. Incidentally, the "peak observed at 545 nm" in this application refers to the maximum peak in which the minimum value is present in a wavelength range of 545±5 nm. Similarly, the "peak observed at 575 nm" in this application refers to the maximum peak in which the minimum value is present in a wavelength range of 575±5 nm. Further, the transmittance of the analysis sample at wavelengths of 545 nm and 575 nm can be decreased by appropriately selecting a refractive index adjuster in consideration of the transmittance of the refractive index adjuster at wavelengths of 545 nm and 575 nm.

Specifically, as for the analysis sample, the transmittance on at least one of the peak observed at 545 nm and the peak observed at 575 nm is preferably 15% or more and more preferably 20% or more. In a further preferred embodiment, as for the analysis sample, the transmittance of both the peak observed at 545 nm and the peak observed at 575 nm is 15% or more. In a particularly preferred embodiment, as for the analysis sample, the transmittance of both the peak observed at 545 nm and the peak observed at 575 nm is 20% or more. The transmittance of both the peak observed at 545 nm and the peak observed at 575 nm is also a value measured at an optical path length of 50 μm, and can also be measured, for example, by the method described in Embodiments.

In a case in which the degree of solubility of the refractive index adjuster is high, there is an advantage that the refractive index can be widely adjusted. Therefore, a refractive index adjuster having a high solubility is preferable. For example, a refractive index adjuster having a degree of solubility of more than 50 mM with respect to water at 20° C. may be used. The degree of solubility of the refractive index adjuster with respect to water at 20° C. is preferably 100 mM or more, more preferably 200 mM or more, more preferably 400 mM or more, and particularly preferably 1000 mM or more. The upper limit of the degree of solubility of the refractive index adjuster is not particularly limited, and a higher degree of solubility is preferable. For example, the degree of solubility may be about 2 M.

Specific examples of the refractive index adjuster may include a dye or chromogen as represented by the following Formula (1), and an aromatic hydrocarbon compound having an ionic functional group such as a tetrazolium salt having a benzothiazoyl group, polysaccharide, sugar alcohol, or a benzenesulfonic acid compound, having a degree of solubility of 200 mM or more with respect to water. These compounds may be in the form of a salt, more specifically, may be a sodium salt, a potassium salt, an ammonium salt, a methylamine salt, an ethylamine salt, a diethylamine salt, a triethylamine salt, a monoethanolamine salt, and halides such as a chloride, but the compounds are not limited thereto. The salt is preferably a sodium salt or a potassium salt.

Among them, from the viewpoint of the detection accuracy of an analyte, the refractive index adjuster is preferably one or more kinds selected from the group consisting of a compound represented by the following Formula (1), a benzenesulfonic acid compound, a disaccharide, and salts thereof:

[Chem. 1]

  Formula (1)

provided that, in the above Formula (1), $Q^1$ and $Q^2$ each independently represent an aryl group or nitrogen-containing heterocyclic group that may have one or more substituents; and the substituents are selected from the group consisting of a halogen atom, a hydroxy group, an alkyl group having 1 to 3 carbon atoms, an alkoxy group having 1 to 3 carbon atoms, a carboxy group, a sulfo group, an amino group, a carbamoyl group, a sulfamoyl group, a phenyl group, a carboxyphenyl group, and a sulfophenyl group.

Examples of the "aryl group" in the compound represented by Formula (1) may include a phenyl group, a naphthyl group, an anthracenyl group, and a phenanthryl group, and the aryl group is preferably selected from the group consisting of a phenyl group and a naphthyl group.

Examples of the "nitrogen-containing heterocyclic group" in the compound represented by Formula (1) may include a pyrrolidyl group, a pyrrolyl group, a piperidyl group, a pyridyl group, an imidazoyl group, a pyrazole group, a pyrazolonyl group, an oxazoyl group, a thiazoyl group, a pyrazyl group, an indoyl group, an isoindoyl group, and a benzimidazoyl group, and preferably, the nitrogen-containing heterocyclic group is selected from the group consisting of an imidazoyl group, a pyrazole group, and a pyrazolonyl group.

The aryl group or the nitrogen-containing heterocyclic group may have one or more substituents selected from the group consisting of a halogen atom (for example, a fluorine atom, a chlorine atom, a bromine atom, and an iodine atom), a hydroxy group, an alkyl group having 1 to 3 carbon atoms (for example, a methyl group, an ethyl group, a n-propyl group, and an isopropyl group), an alkoxy group having 1 to 3 carbon atoms (for example, a methoxy group, an ethoxy group, a n-propoxy group, and an isopropoxy group), a carboxy group, a sulfo group, an amino group, a carbamoyl group, a sulfamoyl group, a phenyl group, a carboxyphenyl group, and a sulfophenyl group. Further, the phenyl group that is the substituent of the aryl group or the nitrogen-containing heterocyclic group may be further substituted with one or more substituents selected from the group consisting of the halogen atom (for example, a fluorine atom, a chlorine atom, a bromine atom, and an iodine atom), the hydroxy group, the alkyl group having 1 to 3 carbon atoms (for example, a methyl group, an ethyl group, a n-propyl group, and an isopropyl group), the alkoxy group having 1 to 3 carbon atoms (for example, a methoxy group, an ethoxy group, a n-propoxy group, and an isopropoxy group), the carboxy group, the sulfo group, the amino group, the carbamoyl group, the sulfamoyl group, the phenyl group, the carboxyphenyl group, and the sulfophenyl group, which are described above.

From the viewpoint of detecting an analyte with high accuracy, in a preferred embodiment, $Q^1$ is represented by the following formula:

[Chem. 2]

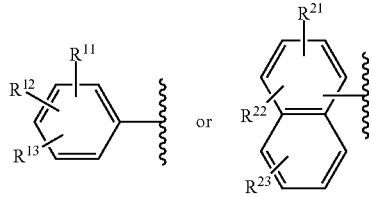

provided that, $R^{11}$, $R^{12}$, $R^{13}$, $R^{21}$, $R^{22}$, and $R^{23}$ are each independently selected from the group consisting of a hydrogen atom, a halogen atom, a carboxy group, a carboxylic acid salt group, a sulfo group, a sulfonic acid salt group, a carbamoyl group, and a sulfamoyl group.

From the viewpoint of detecting an analyte with high accuracy, in a preferred embodiment, $Q^2$ is represented by the following formula:

[Chem. 3]

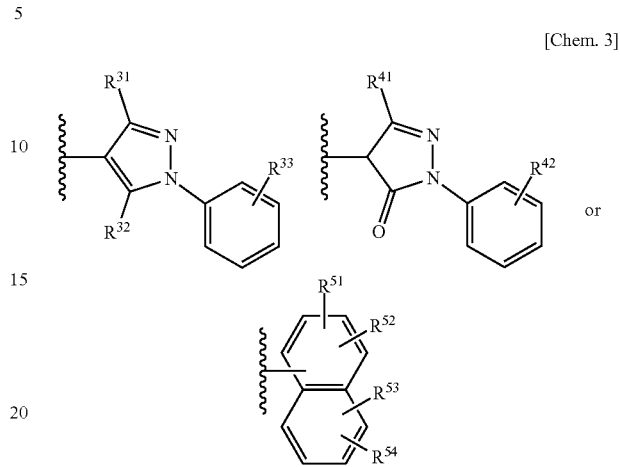

provided that, $R^{31}$, $R^{32}$, and $R^{41}$ are each independently selected from the group consisting of a hydrogen atom, a hydroxy group, an alkyl group having 1 to 3 carbon atoms, a carboxy group, a carboxylic acid salt group, a sulfo group, a sulfonic acid salt group, an amino group, a carbamoyl group, and a sulfamoyl group; $R^{33}$ and $R^{42}$ are each independently selected from the group consisting of a hydrogen atom, a carboxy group, a carboxylic acid salt group, a sulfo group, and a sulfonic acid salt group; and $R^{51}$, $R^{52}$, $R^{53}$, and $R^{54}$ are each independently selected from the group consisting of a hydrogen atom, a halogen atom, a hydroxy group, a carboxy group, a carboxylic acid salt group, a sulfo group, a sulfonic acid salt group, a carbamoyl group, and a sulfamoyl group.

In a more preferred embodiment, $Q^2$ is represented by the following formula:

[Chem. 4]

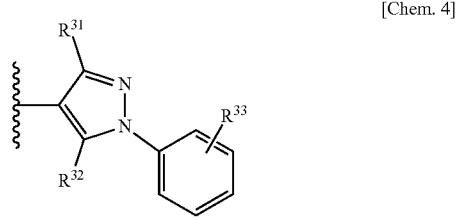

provided that, $R^{31}$, $R^{32}$, and $R^{33}$ are as described above.

In a preferred embodiment, the compound represented by Formula (1) is represented by the following formula:

[Chem. 5]

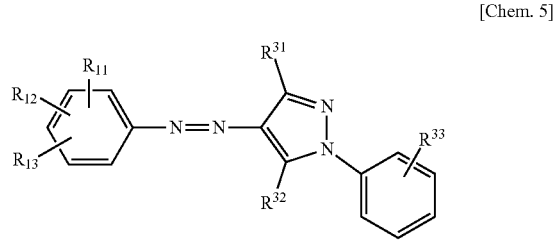

-continued

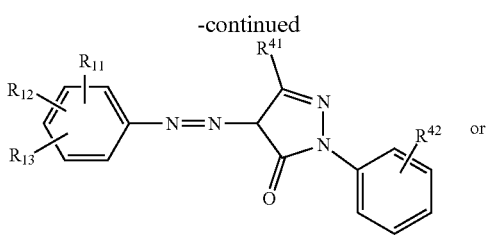

or

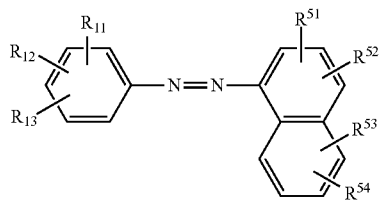

provided that, $R^{11}$, $R^{12}$, $R^{13}$, $R^{31}$, $R^{32}$, $R^{33}$, $R^{41}$, $R^{42}$, $R^{51}$, $R^{52}$, $R^{53}$, and $R^{54}$ are as described above.

More specific examples of the compound represented by the above Formula (1) may include Acid Yellow 11, Acid Yellow 23, Acid Yellow 49, Acid Yellow 59, Acid Orange 12, Orange G, Acid Red 18, Acid Red 26, Acid Red 27, Acid Red 88, Solvent Yellow 5, Solvent Yellow 6, Solvent Yellow 11, Food Yellow 3, and Food Yellow 5. Among them, a compound selected from the group consisting of Acid Yellow 11, Acid Yellow 23, Acid Yellow 49, Acid Yellow 59, and Food Yellow 3 is preferably used. In a more preferred embodiment, Acid Yellow 23 is used as the refractive index adjuster.

Examples of the benzenesulfonic acid compound used as the refractive index adjuster may include benzenesulfonic acid, 1,2-benzene disulfonic acid, 1,3-benzene disulfonic acid, 1,4-benzene disulfonic acid, 1,2,4-benzenetrisulfonic acid, and 1,3,5-benzenetrisulfonic acid. Among them, the benzenesulfonic acid compound is preferably selected from the group consisting of 1,2-benzene disulfonic acid, 1,3-benzene disulfonic acid, and 1,4-benzene disulfonic acid, and is more preferably 1,3-benzene disulfonic acid.

Examples of the disaccharide used as the refractive index adjuster may include sucrose, maltose, isomaltose, lactose, trehalose, sucralose, cellobiose, lactulose, turanose, galactosucrose, trehalosamine, maltitol, and lactitol, but the disaccharide is not limited thereto. As the disaccharide, non-reducing sugar such as sucrose, trehalose, sucralose, galactosucrose, trehalosamine, maltitol, or lactitol is preferable, and more preferably, trehalose and/or sucralose is used. In particular, sucralose having a low osmotic pressure is preferable in that sucralose has a large effect of suppressing contraction of a red blood cell and can be dissolved more in the analysis sample.

The amount of the refractive index adjuster to be dissolved in the analysis sample is, for example, 200 to 1500 (mmol/L extra-red blood cell fluid), preferably 300 to 1500 (mmol/L extra-red blood cell fluid), and more preferably 330 to 800 (mmol/L extra-red blood cell fluid). With such an amount, scattering light can be more effectively suppressed and the analyte can be detected with higher accuracy. Incidentally, the amount of the refractive index adjuster is a value obtained by the calculation method described in Embodiments.

In the method according to the aspect of the present disclosure, the detection of the analyte is performed by a colorimetric method. In an embodiment, the detection method includes performing a chromogenic reaction by dissolving a coloring reagent in the blood sample or the analysis sample, and the detection of the analyte is performed on the basis of color intensity by the chromogenic reaction. For example, the detection of the analyte can be performed on the basis of color intensity of the coloring reagent in an absorption peak by the chromogenic reaction.

The coloring reagent is not particularly limited, and for example, a coloring reagent that is conventionally used for detecting various analytes in the blood sample can be used. In a preferred embodiment, the coloring reagent has an absorption peak wavelength in a wavelength range of 550 to 750 nm, and in more preferred embodiment, the coloring reagent has an absorption peak wavelength in a wavelength range of 600 nm or more and less than 700 nm.

More specific examples of the coloring reagent may include a tetrazolium salt; a combination of a coupler such as 4-aminoantipyrine (4AA), 3-methyl-2-benzothiazolinonehydrazone (MBTH) or 2-hydrazone-2,3-dihydro-3-methyl-6-benzothiazolesulfonic acid (SMBTH) and a Trinder's reagent such as an aniline compound or phenol that will be described later; a diphenylamine-based chromogen such as a N-(carboxymethyl aminocarbonyl)-4,4'-bis(dimethylamino)diphenylamine sodium salt (DA-64); and a phenothiazine-based chromogen such as a 10-(carboxymethyl aminocarbonyl)-3,7-bis(dimethylamino)phenothiazine sodium salt (DA-67). Among the coloring reagents, from the viewpoint of measurement accuracy, a tetrazolium salt is preferably used.

The "tetrazolium salt" may be in the form of a fluoride, a chloride, a bromide, an iodide, a sodium salt, a potassium salt, an ammonium salt, a methylamine salt, an ethylamine salt, a diethylamine salt, a triethylamine salt, a monoethanolamine salt, or the like. More specific examples of the tetrazolium salt include a 2-(4-iodophenyl)-3-(4-nitrophenyl)-5-(2,4-disulfophenyl)-2H-tetrazolium salt, a 2-(4-iodophenyl)-3-(2,4-dinitrophenyl)-5-(2,4-disulfophenyl)-2H-tetrazolium salt, a 2-benzothiazolyl-3-(4-carboxy-2-methoxyphenyl)-5-[4-(2-sulfoethylcarbamoyl)phenyl]-2H-tetrazolium salt, a 2,2'-dibenzothiazolyl-5,5'-bis[4-di(2-sulfoethyl)carbamoylphenyl]-3,3'-(3,3'-dimethoxy 4,4'-biphenylene)ditetrazolium salt, a 2-(2-methoxy-4-nitrophenyl)-3-(4-nitrophenyl)-5-(2,4-disulfophenyl)-2H-tetrazolium salt, a 2-(4-nitrophenyl)-5-phenyl-3-[4-(4-sulfophenylazo)-2-sulfophenyl]-2H-tetrazolium, a 2-(4-iodophenyl)-3-(4-nitrophenyl)-5-phenyl-2H-tetrazolium salt, a 3-(4,5-dimethyl-2-thiazolyl)-2,5-diphenyl-2H-tetrazolium salt, a 2,3-bis-(2-methoxy-4-nitro-5-sulfophenyl)-2H-tetrazolium-5-carboxanilide salt, and a 2,2'-di(4-nitrophenyl)-5,5'-diphenyl-(3,3'-dimethoxy)-4,4'-bisphenylene ditetrazolium salt. Among these, a tetrazolium salt having a benzothiazolyl structure is more preferable, and a 2-benzothiazolyl-3-(4-carboxy-2-methoxyphenyl)-5-[4-(2-sulfoethylcarbamoyl)phenyl]-2H-tetrazolium sodium salt (WST-4) is preferable.

The chromogenic reaction using the tetrazolium salt may be, for example, reaction using an oxidoreductase described later. For example, in a case in which the analyte is glucose and glucose dehydrogenase (GDH) described later is used, glucose can be quantitatively detected by measuring an absorbance at an absorption wavelength (for example, an absorption peak wavelength) by formazan generated by the following reaction mechanism.

[Chem. 6]

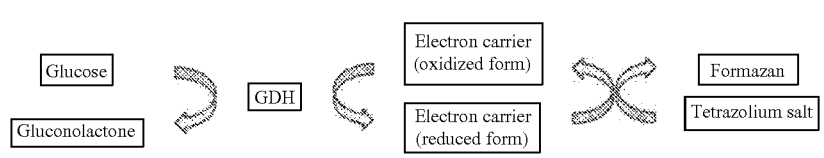

In this application, the analyte is not particularly limited, and for example, can be suitably used in detection of glucose, cholesterol, neutral fat, nicotinamide adenine dinucleotide phosphate (NADPH), nicotinamide adenine dinucleotide (NADH), lactic acid, alcohol, uric acid, or the like. Among these, according to a preferred embodiment of the present disclosure, the analyte is selected from the group consisting of glucose, cholesterol, neutral fat, nicotinamide adenine dinucleotide phosphate, nicotinamide adenine dinucleotide, and uric acid.

<Composition for Detecting Analyte in Blood Sample>

Another aspect of the present disclosure relates to a composition for detecting an analyte in a blood sample, the composition containing a coloring reagent, an oxidoreductase, and a refractive index adjuster.

As the coloring reagent and the refractive index adjuster contained in the composition, the coloring reagent and the refractive index adjuster described above can be used.

The content of the refractive index adjuster in the composition is not particularly limited, but the refractive index adjuster is blended at a ratio of 0.1 to 10 mol with respect to 1 mol of the coloring reagent. From the viewpoint of the effect of further reducing a difference in refractive index between a red blood cell and an extra-red blood cell fluid, the refractive index adjuster is blended at a ratio of preferably 0.1 to 8 mol and more preferably 0.2 to 4 mol with respect to 1 mol of the coloring reagent.

The oxidoreductase contained in the composition is not particularly limited, but can be suitably selected according to the type of analyte. Specific examples of the oxidoreductase include glucose dehydrogenase (GDH) (for example, glucose dehydrogenase (PQQ-GDH) having pyrroloquinoline quinone (PQQ) as a coenzyme, glucose dehydrogenase (GDH-FAD) having flavin adenine dinucleotide (FAD) as a coenzyme, glucose dehydrogenase (GDH-NAD) having nicotinamide adenine dinucleotide (NAD) as a coenzyme, glucose dehydrogenase (GDH-NADP) having nicotine adenine dinucleotide phosphate (NADP) as a coenzyme, and the like), glucose oxidase (GOD), glucose-6-phosphate dehydrogenase, cholesterol dehydrogenase, cholesterol oxidase, glycerophosphate dehydrogenase, glycerophosphate oxidase, lactate dehydrogenase (LDH), lactate oxidase, alcohol dehydrogenase, alcohol oxidase, uricase, and urate dehydrogenase. Herein, the oxidoreductase may be used alone or in combination of two or more kinds thereof. For example, in a case in which a biogenic component is glucose, the oxidoreductase is preferably glucose dehydrogenase or glucose oxidase. Further, in a case in which a biogenic component is cholesterol, the oxidoreductase is preferably cholesterol dehydrogenase or cholesterol oxidase. Herein, the oxidoreductase may be used alone or in combination of two or more kinds thereof.

For example, in a case in which an analyte is glucose, the oxidoreductase is preferably glucose dehydrogenase or glucose oxidase. In a case in which an analyte is cholesterol, the oxidoreductase is preferably cholesterol dehydrogenase or cholesterol oxidase. In a case in which an analyte is neutral fat, the oxidoreductase is preferably glycerophosphate dehydrogenase or glycerophosphate oxidase. In addition to the oxidoreductase, other enzymes such as diaphorase, peroxidase, lipo-protein lipase, and glycerol kinase may be used in combination according to the analyte or the chromogenic reaction mechanism.

The content of the oxidoreductase in the composition is also not particularly limited, but can be appropriately set according to an enzyme to be used. For example, the content of the oxidoreductase is $1 \times 10^3$ to $5 \times 10^7$ μkat (that is, $6 \times 10^6$ to $3 \times 10^9$ U), preferably $5 \times 10^5$ to $1 \times 10^7$ μkat (that is, $3 \times 10^7$ to $6 \times 10^8$ U), and more preferably $1 \times 10^6$ to $5 \times 10^6$ μkat (that is, $6 \times 10^7$ to $3 \times 10^8$ U) with respect to 1 mol of the coloring reagent.

The composition may contain an electron carrier as necessary. Examples of the electron carrier that may be used in the composition include phenazine methosulfate (PMS), 1-methoxy-5-methylphenazinium methyl sulfate (m-PMS), Meldola's blue, diaphorase, dichlorophenolindophenol, potassium ferricyanide, ferrocene, a ruthenium complex, an osmium complex, and benzoquinone, but the electron carrier is not limited thereto. A combination of the oxidoreductase and the electron carrier is not particularly limited, but may be appropriately set according to the object. Examples thereof may include a combination of GDH/phenazine methosulfate, a combination of GDH/1-methoxy-5-methylphenazinium methyl sulfate, a combination of GDH/potassium ferricyanide, a combination of GDH/a ruthenium complex, a combination of GOD/potassium ferricyanide, a combination of cholesterol dehydrogenase/ferrocene, and a combination of glycerophosphate dehydrogenase/diaphorase.

The content of the electron carrier in the composition is also not particularly limited, but for example, is $1 \times 10^{-3}$ to 1 mol, preferably $2 \times 10^{-3}$ to $1 \times 10^{-1}$ mol, and more preferably $1 \times 10^{-2}$ to $5 \times 10^{-2}$ mol, with respect to 1 mol of the coloring reagent.

The composition may contain coenzymes as necessary. Examples of the coenzyme that may be used in the composition include pyrroloquinoline quinone (PQQ), flavin adenine dinucleotide (FAD), nicotinamide adenine dinucleotide (NAD), nicotine adenine dinucleotide phosphate (NADP), and adenosine triphosphate (ATP), but the coenzyme is not limited thereto.

Other than the above, the composition may contain, to the extent that the target effect of the present disclosure is not impaired, buffers (for example, a phosphate buffer, a citrate buffer, a citrate-phosphate buffer, a tris-hydrochloric acid buffer (trishydroxymethyl aminomethane-HCl buffer), an MES buffer (a 2-morpholinoethane sulfonate buffer), a TES buffer (N-tris(hydroxymethyl)methyl-2-aminoethane sulfonate buffer), an acetate buffer, an MOPS buffer (a 3-morpholinopropane sulfonate buffer), an MOPS-NaOH buffer, an HEPES buffer (a 4-(2-hydroxyethyl)-1-piperazine ethanesulfonate buffer), a GOOD buffers such as an HEPES-NaOH buffer, an amino acid-based buffer such as a glycine-hydrochloric acid buffer, a glycine-NaOH buffer, a glycylglycine-NaOH buffer, or glycylglycine-KOH buffer, a boric acid-based buffer such as a tris-boric acid buffer, a boric acid-NaOH buffer, or a boric acid buffer, an imidazole buffer, and the like), enzymes (for example, diaphorase, peroxidase, glucokinase, hexokinase, lipo-protein lipase, glycerol kinase, and the like), aniline compounds (for example, N-(3-sulfopropyl)aniline, N-ethyl-N-(2-hydroxy-3-sulfopropyl)-3-methylaniline, N-ethyl-N-(2-hydroxy-3-sulfopropyl)-3,5-dimethylaniline, N-ethyl-N-(2-hydroxy-3-sulfopropyl)-3-methoxyaniline, N-ethyl-N-(2-hydroxy-3-sulfopropyl)-3,5-dimethoxyaniline, N-ethyl-N-sulfopropyl-3-methylaniline, N-ethyl-N-sulfopropyl-3-methoxyaniline, N-(2-hydroxy-3-sulfopropyl)-3,5-dimethoxyaniline, and the like), phenols (for example, phenol, 4-chlorophenol, 3-methylphenol, 3-dimethylaminobenzoic acid, 3-hydroxy-2,4,6-triiodobenzoic acid, and the like), surfactants, and the like.

The preparation method of the composition is not particularly limited, but a coloring reagent, an oxidoreductase, a refractive index adjuster, and another component that is contained may be mixed by appropriate means. When respective components of the composition are mixed, the mixing may be performed in an appropriate solvent or dispersion medium such as water, methanol, ethanol, glycerin, or dimethylsulfoxide.

<Analyte Detection Chip in Blood Sample>

The third aspect of the present disclosure relates to a chip for detecting an analyte in a blood sample, the chip having a reaction portion including a coloring reagent, an oxidoreductase, and a refractive index adjuster.

Hereinafter, the third aspect of the present disclosure will be described in more detain with reference to FIGS. 1 to 4 using, as an example, an analyte detection chip 12 according to an embodiment of the present disclosure (hereinafter, the analyte detection chip 12 is also simply referred to as the "detection chip 12") and an analyte detection apparatus 10 (hereinafter, the analyte detection apparatus 10 is also simply referred to as the "detection apparatus 10") used in detection of an analyte using the detection chip 12, but the present disclosure is not limited to the following embodiment.

The detection apparatus 10 is formed, as illustrated in FIG. 1, as an apparatus for measuring an analyte (for example, glucose or the like) in a blood sample. The detection apparatus 10 is mainly applied for personal use, operated by a user (examinee). For example, in a case in which the analyte is glucose, the user can measure blood glucose before meal and can manage one's own blood glucose. Further, medical workers can also use the detection apparatus 10 to evaluate a health condition of a subject, and in this case, the detection apparatus 10 may be appropriately modified to be able to be installed at a medical facility, or the like.

The detection apparatus 10 employs a principle of a colorimetric method, in which a content of the analyte in the blood sample is optically measured. In particular, the detection apparatus 10 detects the analyte by a transmission-type measurement unit 14 that emits measurement light of a predetermined wavelength to the analysis sample and receives the light transmitted through the analysis sample.

The detection apparatus 10 is attached with the detection chip 12 in which blood is taken or takes in blood onto the detection chip 12 in a state of being attached with the detection chip 12, and the analyte is detected by the measurement unit 14. The detection chip 12 may be a disposal type that is discarded every time after one-time use for measurement. On the other hand, the detection apparatus 10 is preferably configured as a portable and robust apparatus such that the user can repeat the measurement easily.

Figure 2:
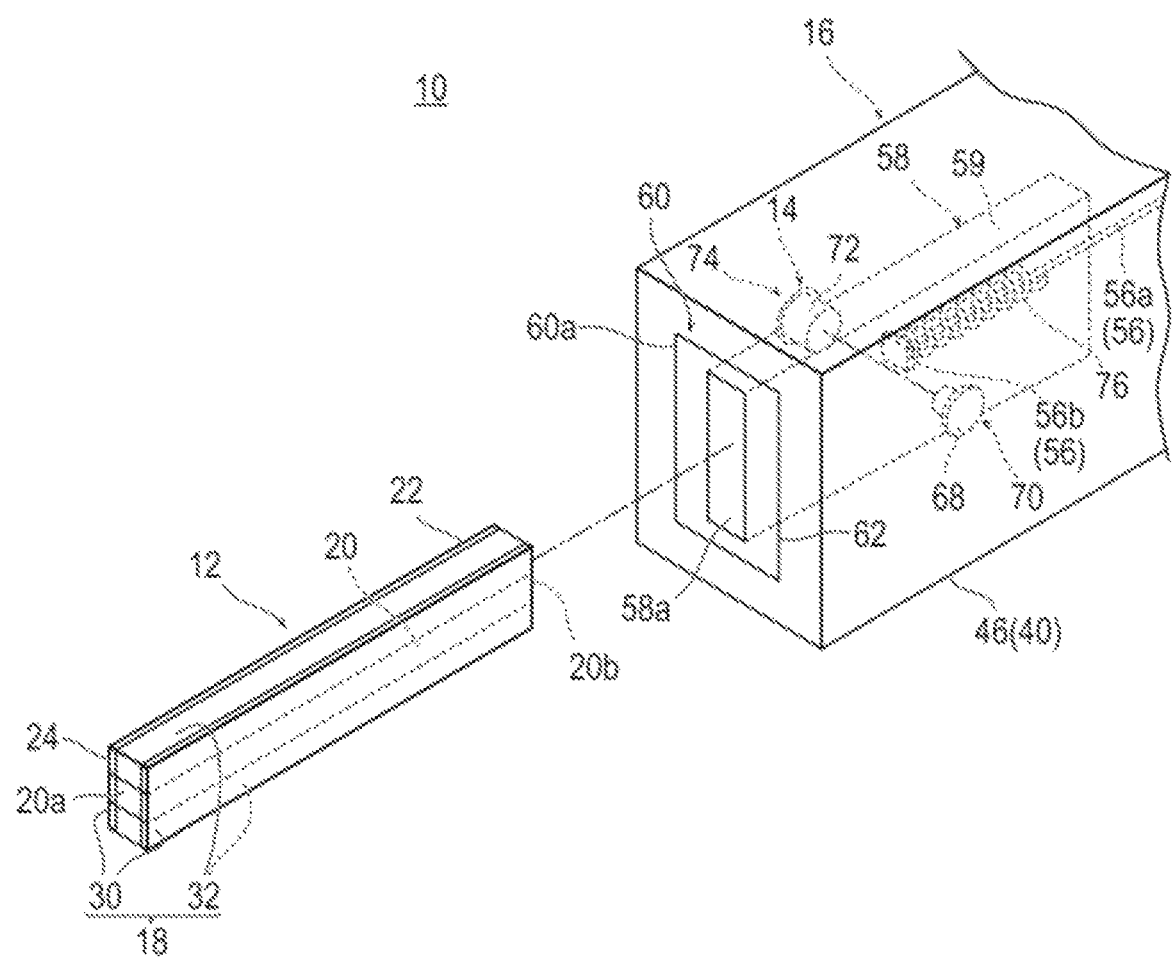
FIG. 2 is a perspective view illustrating the detection chip and a photometric block of an apparatus main body in enlarged scale, illustrated in FIG. 1.

The detection chip 12 includes a chip main body portion 18 having a plate shape and a cavity 20 (liquid-retainable cavity) extending in a surface direction of a plate surface inside the chip main body portion 18, as illustrated in FIG. 2. The detection chip 12 is preferably a glucose detection chip.

The chip main body portion 18 has a rectangular shape, with a long side 22 elongated in the insertion and removal directions of the detection apparatus 10 (distal end and proximal end directions of the detection apparatus 10) in a side view, and a short side 24 shortened in the up-down direction. For example, the length of the long side 22 of the chip main body portion 18 may be set to a length equal to or more than twice the short side 24. With this setting, the detection chip 12 can ensure a sufficient insertion amount with respect to the detection apparatus 10.

Further, the thickness of the chip main body portion 18 is formed to be extremely small (thin) compared with the side surface formed in a rectangular shape (diagram in FIG. 2 is illustrated such that the chip main body portion has a sufficient thickness daringly). For example, the thickness of the chip main body portion 18 is preferably set to $\frac{1}{10}$ or less of the above-described short side 24. The thickness of the chip main body portion 18 may appropriately be designed according to the shape of an insertion hole 58 of the detection apparatus 10.

The detection chip 12 is configured such that the chip main body portion 18 includes a pair of plate pieces 30 and a pair of spacers 32 so as to form the cavity 20.

Figure 3:
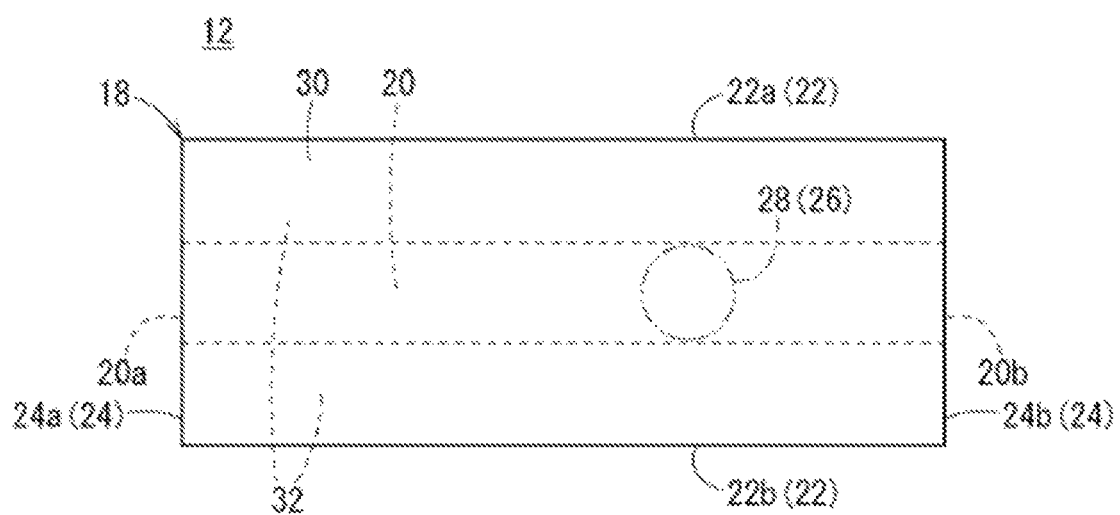
FIG. 3 is a diagram schematically illustrating an embodiment of the detection chip for an analyte.

FIG. 3 is a side view illustrating the detection chip of FIG. 1. Although the corner portions of the chip main body portion 18 are sharp in FIG. 3, the corner portions may be rounded, for example. Further, the shape of the chip main body portion 18 is limited to the thin plate shape, but may be freely designed, of course. For example, the chip main body portion 18 may be formed in a square, other polygons, a circle (including ellipse), or the like, in a side view.

The cavity 20 provided inside the chip main body portion 18 is located at an intermediate position of the chip main body portion 18 in the up-down direction, and formed in a straight line across the longitudinal direction of the chip main body portion 18. The cavity 20 is connected to a distal end port 20a formed at a distal end side 24a of the chip main body portion 18 and a proximal end port 20b formed at a proximal end side 24b of the chip main body portion 18, and communicates with the outside of the chip main body portion 18. The cavity 20 takes in the blood of the user from the distal end port 20a, and can allow the blood to flow along the extending direction on the basis of capillary action. The amount of blood that flows in the cavity 20 is small, and thus, even when the blood moves to the proximal end port 20b, leaking is suppressed by tension. Incidentally, an absorption portion absorbing blood (for example, a spacer 32 formed with a porous body only on the proximal end side, and or like, which will be described) may be provided on the side of the proximal end side 24b of the chip main body portion 18.

Further, at a predetermined position of the cavity 20 (for example, a position slightly close to the proximal end from the intermediate point between the distal end port 20a and the proximal end port 20b, illustrated in FIG. 3), a reaction portion 26 in which chromogenic reaction is performed and a measurement target portion 28 that is measured by the detection apparatus 10 are set. The reaction portion 26 contains a coloring reagent, an oxidoreductase, and a refractive index adjuster. The blood that flows inside cavity 20 in the proximal end direction comes in contact with the reaction portion 26, reagent components of the reaction portion 26 are dissolved in the blood to perform chromogenic reaction, and the blood develops color. Incidentally, in the upper portion of the cavity 20 in the longitudinal direction, the application position of the reaction portion 26 and the measurement target portion 28 may be shifted with each other, and for example, the reaction portion 26 may be provided on the upstream side in the blood flow direction of the measurement target portion 28.

The amount of each reagent component contained in the reaction portion may be appropriately set according to the amount of blood sample used per one measurement (blood amount per chip). Incidentally, the content of each reagent component contained in the reaction portion described below is a value obtained according to the calculation method in Embodiments.

The content of the refractive index adjuster in the reaction portion is, for example, 200 to 1500 (mmol/L extra-red blood cell fluid), preferably 300 to 1500 (mmol/L extra-red blood cell fluid), and more preferably 330 to 800 (mmol/L extra-red blood cell fluid). When the content of the refractive index adjuster in the reaction portion is set within the range as described above, generation of blood cell-derived scattering light is further suppressed and the detection accuracy of the analyte is improved. Incidentally, the refractive index adjuster can be used alone, or as long as the target effect of the present disclosure is achieved, two or more kinds thereof may be used as a mixture. In the case of using two or more kinds of refractive index adjusters, the above-described numerical value range corresponds to the total amount thereof.

The content of the coloring reagent in the reaction portion is, for example, 110 to 825 (mmol/L extra-red blood cell fluid), preferably 165 to 825 (mmol/L extra-red blood cell fluid), and more preferably 180 to 450 (mmol/L extra-red blood cell fluid). Incidentally, the coloring reagent can be used alone, or as long as the target effect of the present disclosure is achieved, two or more kinds thereof may be used as a mixture. In the case of using two or more kinds of coloring reagents, the above-described numerical value range corresponds to the total amount thereof.

The content of the oxidoreductase in the reaction portion is, for example, $3 \times 10^3$ to $2.5 \times 10^6$ (µkat/L extra-red blood cell fluid) (that is, $1.8 \times 10^7$ to $1.5 \times 10^8$ (U/L extra-red blood cell fluid)), preferably $4.5 \times 10^3$ to $2.5 \times 10^6$ (µkat/L extra-red blood cell fluid) (that is, $2.7 \times 10^7$ to $1.5 \times 10^8$ (U/L extra-red blood cell fluid)), and more preferably $5 \times 10^3$ to $1.2 \times 10^6$ (µkat/L extra-red blood cell fluid) (that is, $3 \times 10^7$ to $7.2 \times 10^7$ (U/L extra-red blood cell fluid)). Incidentally, the oxidoreductase can be used alone, or as long as the target effect of the present disclosure is achieved, two or more kinds thereof may be used as a mixture. In the case of using two or more kinds of oxidoreductase, the above-described numerical value range corresponds to the total amount thereof.

The reaction portion may contain an electron carrier according to an oxidoreductase to be used. The content of the electron carrier in the reaction portion is, for example, 2 to 15 (mmol/L extra-red blood cell fluid), preferably 3 to 15 (mmol/L extra-red blood cell fluid), and more preferably 3 to (mmol/L extra-red blood cell fluid). Incidentally, the electron carrier can be used alone. Alternatively, as long as the target effect of the present disclosure is achieved, electron carrier does not have to be added, or two or more kinds thereof may be used as a mixture. In the case of using two or more kinds of electron carriers, the above-described numerical value range corresponds to the total amount thereof.

To the extent that the target effect of the present disclosure is not impaired, in the reaction portion, a reagent other than the coloring reagent, the oxidoreductase, and the refractive index adjuster may be contained, for example, the coenzymes, the buffers (for example, a Tris buffer, a Tricine buffer, an HEPES buffer, a phosphate buffer, an acetate buffer, and the like), enzymes (for example, diaphorase, peroxidase, glucokinase, hexokinase, lipo-protein lipase, glycerol kinase, and the like), aniline compounds (for example, N-(3-sulfopropyl)aniline, N-ethyl-N-(2-hydroxy-3-sulfopropyl)-3-methylaniline, N-ethyl-N-(2-hydroxy-3-sulfopropyl)-3,5-dimethylaniline, N-ethyl-N-(2-hydroxy-3-sulfopropyl)-3,5-dimethoxyaniline, N-ethyl-N-(3-sulfopropyl)-3-methylaniline, N-(2-hydroxy-3-sulfopropyl)-3,5-dimethoxyaniline, and the like), phenols (for example, phenol, 4-chlorophenol, 3-methylphenol, 3-dimethylaminobenzoic acid, 3-hydroxy-2,4,6-triiodobenzoic acid, and the like), surfactants, and the like, which are described above may be contained.

The forming method of the reaction portion 26 is not particularly limited. For example, a coating liquid (for example, the composition according to the second aspect of the present disclosure) containing a coloring reagent, an oxidoreductase, a refractive index adjuster, and, as necessary, other reagents is applied to one or both of the plate pieces 30, and the coating film is dried as necessary, so that the reaction portion can be formed. The coating liquid used in formation of the reaction portion 26 may contain a solvent. Examples of such a solvent may include one or a mixture of two or more selected from water, lower alcohols (for example, methanol, ethanol, 1-propanol, isopropanol, and the like), ketones (for example, acetone, methyl ethyl ketone, methyl isobutyl ketone, diisobutyl ketone, cyclohexanone, diacetonealcohol, and the like), dimethylsulfoxide, and glycerin, but the solvent is not limited thereto.

The detection chip 12 is configured such that the chip main body portion 18 includes a pair of plate pieces 30 and a pair of spacers 32 so as to form the above-described cavity 20. Each of the pair of plate pieces 30 has above-described rectangular shape in a side view and is mutually arranged in the lamination direction. That is, the pair of plate pieces 30 forms both side surfaces (left side surface and right side surface) of the chip main body portion 18. The plate thickness of each of the plate pieces 30 may be set to a very small size, for example, about 5 µm to 50 µm, being equal to each other. The thickness of the two (one set of) plate pieces 30 may be different from each other.

The pair of plate pieces 30 has a strength that would maintain a plate shape and would not allow plastic deformation even when a certain degree of pressing force is applied from a direction orthogonal to the surface direction. Further, each of the plate pieces 30 is configured to be transparent or translucent so as to be able to transmit the measurement light. Furthermore, it is preferable that each of the plate pieces 30 is configured to be a flat plate surface with an appropriate level of hydrophilicity so as to allow the blood to flow inside the cavity 20 (or a coating agent is applied to the plate surface).

Although the material constituting each of the plate pieces 30 is not particularly limited, a thermoplastic resin material, glass, quartz, and the like may be employed. Examples of the thermoplastic resin material include polymeric materials such as polyolefin (for example, polyethylene, polypropylene, or the like), cycloolefin polymer, polyester (for example, polyethylene terephthalate, polyethylene naphthalate, or the like), polyvinyl chloride, polystyrene, ABS resin, acrylic resin, polyamide, and fluororesin, or a mixture of these.

Further, the pair of spacers 32 is arranged to be sandwiched between the pair of plate pieces 30 and firmly bonded to a facing surface of each of the plate pieces 30 by a predetermined joining means (adhesive, or the like). That is, each of the spacers 32 is a member to form the cavity 20 between the pair of plate pieces 30 and the pair of spacers 32 themselves, by being arranged between the pair of plate pieces 30 so as to separate the pair of plate pieces 30 from each other. In this case, the one spacer 32 is arranged to come in contact with an upper long side 22a of the chip main body portion 18 in FIG. 3 and to extend in the distal end and proximal end directions along the upper long side 22a. The other spacer 32 is arranged to come in contact with a lower long side 22b of the chip main body portion 18 in FIG. 3 and to extend in the distal end and proximal end directions along the lower long side 22b.

The material constituting the pair of spacers 32 is not particularly limited, and examples thereof include various thermoplastic elastomers such as styrene-based, polyolefin-based, polyurethane-based, polyester-based, polyamide-based, polybutadiene-based, transpolyisoprene-based, fluoro-rubber-based, and chlorinated polyethylene-based thermoplastic elastomers. Alternatively, other than the thermoplastic elastomers, various materials that are elastically deformable may be employed, or a structural body such as an elastically deformable porous body (for example, sponge) or a double-sided tape may be employed. Further, an adhesive, which bonds the plate pieces 30 by being in a cured state or a semi-cured state between the pair of plate pieces 30, may be employed as the spacer 32 on one or both surfaces of the base. Furthermore, the spacer 32 may have a configuration in which the spacer 32 contains the reaction portion 26 so that the reaction portion 26 is eluted in the cavity 20 according to inflow of the blood sample.

The plate piece 30 and the spacer 32 may be subjected to the hydrophilization treatment. Examples of the hydrophilization treatment method include a method of applying an aqueous solution containing a hydrophilic polymer such as polyacrylic acid, polyvinylpyrrolidone, or polyacrylamide, in addition to a surfactant, polyethylene glycol, polypropylene glycol, hydroxypropylcellulose, and water-soluble silicone, by a dipping method or a spray method, and methods such as plasma irradiation, glow discharge, corona discharge, and ultraviolet irradiation, and these methods may be used alone or in combination.

The distance between the pair of plate pieces 30 formed by the spacers 32 is, for example, 5 µm to 200 µm and preferably 10 µm to 100 µm.

The detection chip 12 is configured as above. Next, the apparatus main body 16 of the detection apparatus 10 will be described.

As illustrated in FIG. 1, the detection apparatus 10 includes a housing 40 that represents an external view of the detection apparatus. The housing 40 includes a box portion 44 and a photometric block 46. The box portion 44 is formed in a size easily grasped and operated by the user, and contains therein a control unit 42 of the detection apparatus 10. The photometric block 46 has a cylindrical shape, protrudes from a side (distal end side) of the box portion 44 in the distal end direction, and contains therein the measurement unit 14 that is an optical system. Further, a power button 48, an operation button 50, and a display 52 are provided on an upper surface of the box portion 44, and an eject lever 54 is provided on an upper surface of the photometric block 46.

The power button 48 switches start and stop of the detection apparatus 10 according to user operation. The operation button 50 functions as an operation unit that, on the basis of the user operation, performs measurement and display of an analyte, switches display of measurement results (including past measurement result), or the like, on the detection apparatus 10 after being started. The display 52 is formed with liquid crystal, organic EL, or the like, and displays information to be provided to the user in measurement operations such as display of measurement results and display of errors.

The eject lever 54 is movably provided in the distal end and proximal end directions, and releases the lock of an eject pin 56 provided inside the photometric block 46 so as to enable the eject pin 56 to move in the distal end direction (see FIG. 2).

Meanwhile, the photometric block 46 of the apparatus main body 16 is elongated to extend from the box portion 44 in the distal end direction so as to press the distal end to the user's finger, or the like. As illustrated in FIG. 2, the photometric block 46 includes a chip mounting portion 60 including an insertion hole 58, and the measurement unit 14 optically detecting an analyte in the blood.

Figure 4A:
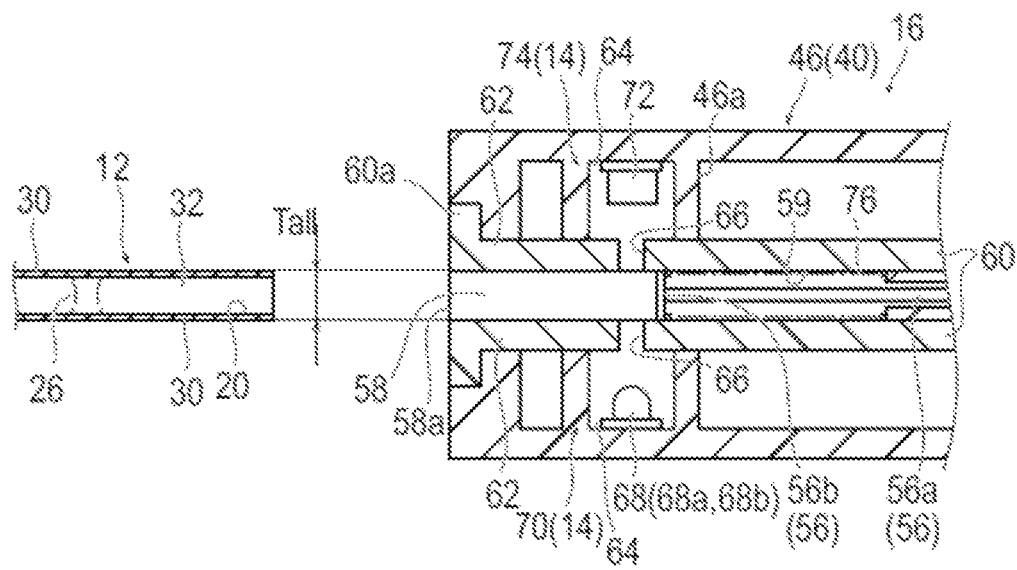
FIG. 4A is a first plan view illustrating attachment operation of the detection chip with the apparatus main body, illustrated in FIG. 1.
Figure 4B:
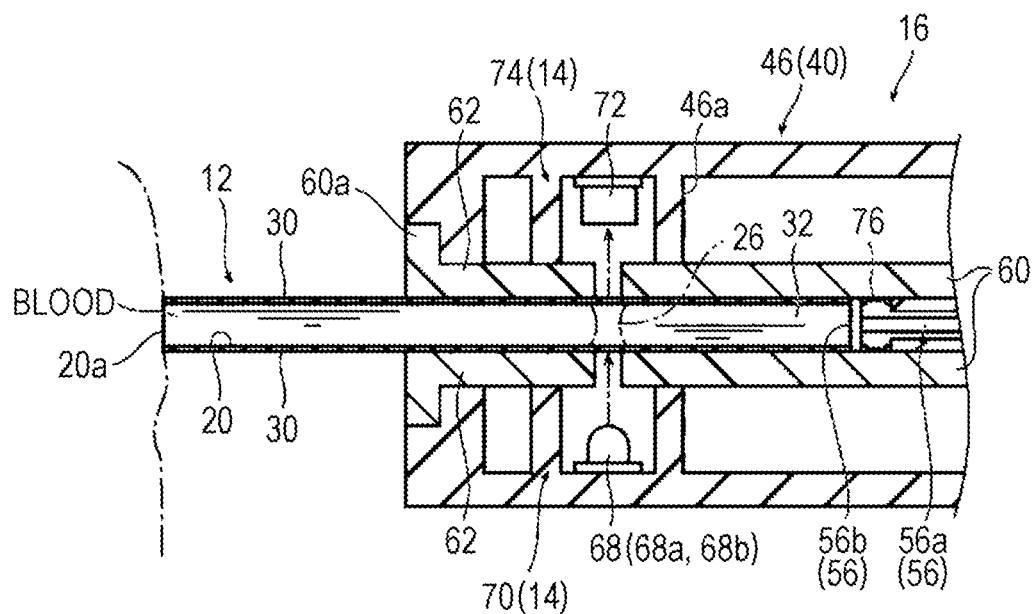
FIG. 4B is a second cross-sectional plan view illustrating attachment operation following the operation in FIG. 4A.

The chip mounting portion 60 includes, at the distal end side, a flange portion 60a that is formed of a material (for example, stainless steel) with high hardness (rigidity) and that protrudes in the outer direction. The chip mounting portion 60 has a cylindrical shape having a predetermined length in the axial direction. The chip mounting portion 60 is positioned and fixed across a distal end surface and an axis center portion (central portion) of the photometric block 46 formed by a resin material. A fixing wall 46a that firmly fixes the chip mounting portion 60 is protrudingly formed at an inner surface of the photometric block 46, as illustrated in FIG. 4A.

The material constituting the chip mounting portion 60 is a material that is hard, unlikely to be easily changed in dimensions, unlikely to be easily worn after repetitive insertion/removal of the detection chip 12, and can be processed with high dimensional accuracy. Examples of the material include metal such as stainless steel or titanium, alumite coating-processed aluminum, liquid crystal polymer, plastic to which a filler such as glass or mica is added, plastic having a surface cured coated with nickel-plating, etc., carbon fiber, and fine ceramics. Among these, by employing metallic materials, it is possible to easily mold the insertion hole 58 with high dimensional accuracy in the manufacture (injection molding, press molding, or the like) of the chip mounting portion 60. Incidentally, the apparatus main body 16 may be configured to be integrally formed with the chip mounting portion 60 by forming the photometric block 46 itself of a hard material (for example, metallic materials).

At the axis center portion of the chip mounting portion 60, the insertion hole 58 is provided by being enclosed by a wall portion 62 of the chip mounting portion 60. The insertion hole 58 has a cross-sectional rectangular shape that is long in the up-down direction and short in the right-left width direction. The insertion hole 58 has a predetermined depth across a portion from the distal end surface toward the inner portion (proximal end direction) in a state where the chip mounting portion 60 is fixed to the photometric block 46.

An insertion opening portion 58a, which is connected to the insertion hole 58 and communicates with the outside, is formed at the distal end side of the chip mounting portion 60.

The dimension of the insertion opening portion 58a in the up-down direction corresponds to the dimension (length in the up-down direction) of the short side 24 of the detection chip 12. Further, the dimension of the insertion opening portion 58a in the right-left width direction, namely, an interval of a pair of wall portions 62 constituting a side surface of the insertion hole 58 is substantially the same as the thickness (Tall in FIG. 4A) of the measurement chip 12 in the lamination direction, as illustrated in FIG. 4A.

As illustrated in FIG. 4A, the chip mounting portion 60 has a pair of element storage spaces 64 in cooperation with the fixing wall 46a of the photometric block 46 in a halfway position where the insertion hole 58 (the measurement hole portion 59) extends. The pair of element storage spaces 64 is a portion of the measurement unit 14, provided at mutually facing positions sandwiching the insertion hole 58. The pair of element storage spaces 64 communicates with the measurement hole portion 59 via each of the light guide portions 66 formed by the chip mounting portion 60.

The measurement unit 14 constitutes a light emitting portion 70 by storing a light emitting element 68 in one element storage space 64, and constitutes a light receiving portion 74 by storing a light receiving element 72 in the other element storage space 64. The light guide portion 66 of the chip mounting portion 60 is formed into a circular hole with a suitable diameter, and thus, functions as a so-called aperture.

The light emitting element 68 of the light emitting portion 70 includes a first light emitting element 68a that emits measurement light having a first wavelength onto the detection chip 12, and a second light emitting element 68b that emits measurement light having a second wavelength different from the first wavelength onto the detection chip 12 (not illustrated in FIG. 2). The first light emitting element 68a and the second light emitting element 68b are arranged in parallel at positions facing the light guide portion 66 of the element storage space 64.

The light emitting elements 68 (the first and second light emitting elements 68a and 68b) can be constituted with light emitting diodes (LED). The first wavelength is a wavelength for detecting color-developing concentration of a reagent 26 according to the amount of blood glucose, that is, for example, 600 nm to 680 nm. The second wavelength is, for example, a wavelength for detecting red blood cell concentration in blood, that is, for example, 510 nm to 540 nm. The control unit 42 inside the box portion 44 supplies a drive current so as to cause each of the first and second light emitting elements 68a and 68b to emit light at predetermined timing. In this case, a measurement value obtained from the color-developing concentration is corrected using a hematocrit value obtained from the red blood cell concentration to obtain the content of an analyte (for example, a blood glucose value). Incidentally, noise caused by a blood cell may be corrected by further performing measurement with other measurement wavelength.

The light receiving portion 74 arranges one light receiving element 72 at a position facing the light guide portion 66 of the element storage space 64. The light receiving portion 74 receives transmitted light from the detection chip 12, and can be configured with a photodiode (PD), for example.

Further, the eject pin 56 (eject portion) joined with the eject lever 54 is provided at a bottom portion (proximal end surface) of the insertion hole 58. The eject pin 56 includes a stick portion 56a that extends in the axis direction of the photometric block 46, and a receiving portion 56b that has a large diameter outwardly in the diameter direction at the distal end portion of the stick portion 56a. The proximal end side 24b of the detection chip 12 inserted into the insertion hole 58 comes in contact with the receiving portion 56b. Further, a coil spring 76 that encloses the eject pin 56 in a non-contact state is provided between the bottom portion of the insertion hole 58 and the receiving portion 56b of the eject pin 56. The coil spring 76 elastically supports the receiving portion 56b of the eject pin 56.

The eject pin 56 is displaced in the proximal end direction when the receiving portion 56b is pressed with insertion of the detection chip 12 by a user, and locked (fixed) by a locking mechanism (not illustrated) provided inside the housing 40. The coil spring 76 elastically contracts according to the displacement of the receiving portion 56b. Further, when the eject pin 56 slightly moves by operation of the eject lever 54 by the user, the locking of the locking mechanism is released, and the eject pin 56 slides in the distal end direction by an elastic restoring force of the coil spring 76. With this operation, the detection chip 12 is pushed by the eject pin 56 and taken out from the insertion hole 58.

Returning to FIG. 1, the control unit 42 of the apparatus main body 16 includes a control circuit having a calculation unit, a storage unit, and an input/output unit (not illustrated). A known computer can be employed as the control unit 42. The control unit 42 detects and calculates an analyte, for example, by performing driving control of the measurement unit 14 according to user operation of the operation button 50, and displays a calculated value (the content of the analyte) on the display 52.

For example, in the detection apparatus 10 that measures an analyte (for example, glucose) by transmitting measurement light to the detection chip 12, the control unit 42 calculates a result of measurement on the basis of the Beer-Lambert law indicated in the following Formula (A).

$$\log_{10}(l_1/l_0) = -\alpha L \qquad (A)$$

In the above Formula (A), $l_0$ represents an light intensity of before incidence into the blood sample, $l_1$ represents an intensity of light after being emitted from the blood sample, a represents an absorption coefficient, and L represents a distance (cell length) for which the measurement light passes.

EMBODIMENTS

The effect of the present disclosure will be described by means of the following Embodiments and Comparative Embodiments. However, the technical scope of the present disclosure is not intended to be limited only to the following Embodiments.

<Refractive Index Increasing Capability of Refractive Index Adjuster>

Aqueous solutions prepared to have a plurality of concentrations within a range of 0 to 350 mg/ml were prepared for the respective refractive index adjusters. The refractive index of each aqueous solution was obtained with a refractometer PAL-RI (ATAGO CO., LTD.). A graph was created in which the concentration of each aqueous solution is plotted on the horizontal axis and the refractive index is plotted for each refractive index adjuster on the vertical axis, and the inclination of the approximate straight line was obtained (a value of "Refractive index increasing capability" in Table 1 indicates an increase amount of the refractive index per 1 [mg/ml], and a larger inclination indicates higher refractive index increasing capability of the refractive index adjuster). The results thereof are presented in Table 1.

Incidentally, "unmeasurable" in Table 1 means that an aqueous solution could not be prepared due to generation of precipitates.

<Red Blood Cell Reducing Capability of Refractive Index Adjuster>

400 μL of blood plasma was recovered from 1.0 ml of blood sample (hematocrit value: 40). A refractive index adjuster was added to 400 μL of the recovered blood plasma to have a concentration of 125 mM. The blood plasma after addition of the refractive index adjuster combined with the original blood sample and mixed by inverting (the concentration of the refractive index adjuster in the blood sample becoming 50 mM). The sample after 5 minutes from mixing by inverting was filled in a hematocrit tube and was separated by centrifugation with a hematocrit centrifuge at $11 \times 10^3$ rpm for 5 minutes. A hematocrit value (Ht) after separation by centrifugation was read. A hematocrit value change amount (ΔHt) was obtained by subtracting the hematocrit value (Ht) after separation by centrifugation from the hematocrit value (=40) before the addition of the refractive index adjuster (a larger ΔHt indicates that the red blood cell reducing capability of the refractive index adjuster is higher). The results thereof are presented in Table 1. Incidentally, "unmeasurable" in Table 1 means that the degree of solubility of the refractive index adjuster was low so that measurement could not be performed.

<Spectrum Analysis>

Figure 6:
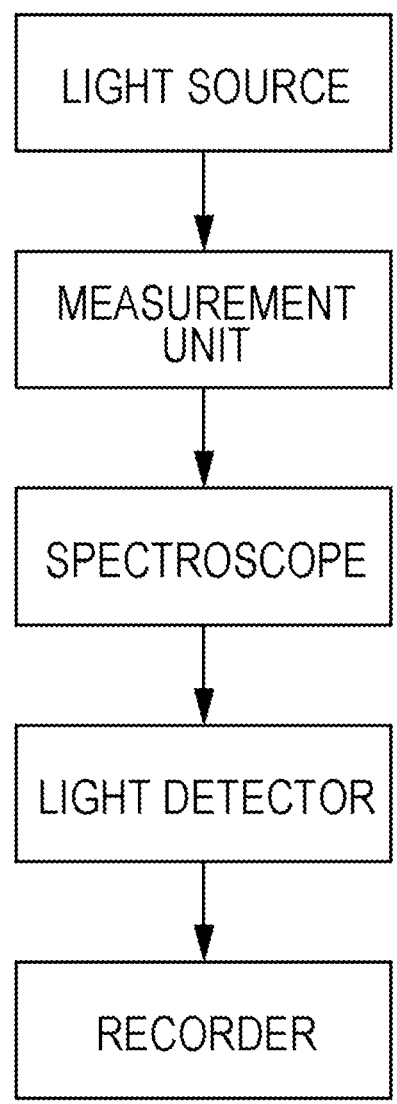
FIG. 6 illustrates an outline of an evaluation system used in spectrum analysis of Embodiments.

The outline of an evaluation system used in spectrum analysis will be described below. Further, the outline of the evaluation system is illustrated in FIG. 6.

Light source: Halogen light source SPL-2H (KLV Co., Ltd.)

Fiber connector: SMA

Conforming fiber: Core diameter=200μ or more

Spectrometer: Small fiber optical spectrometer USB2000+(Ocean Optics, Inc.)

Detector range: 200 to 1100 nm

Figure 7A:
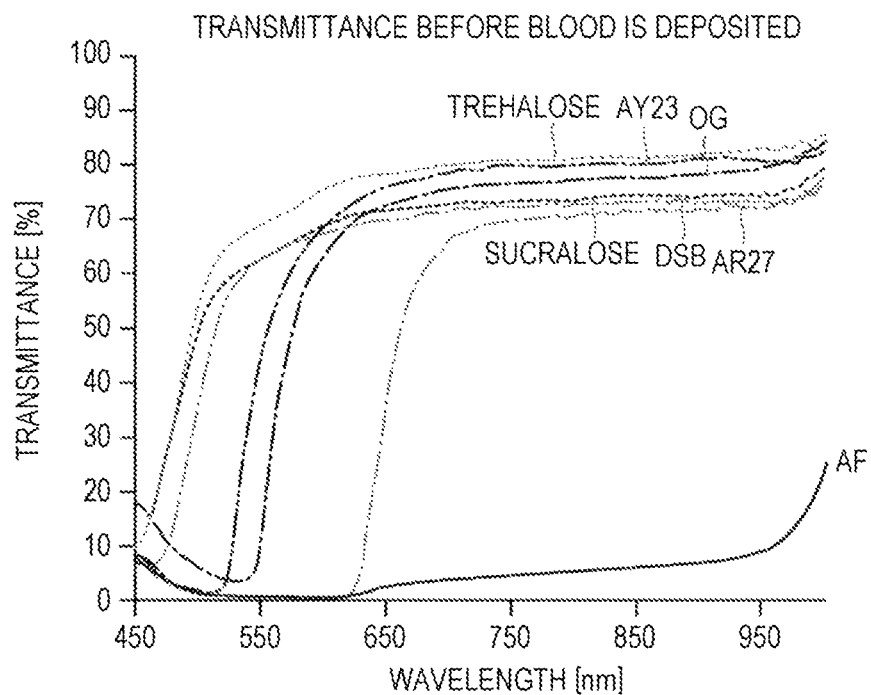
FIG. 7A shows transmittance curves (before blood is deposited) obtained by spectrum analysis of Embodiments and Comparative Embodiments.

The spectrum analysis was performed using the blood glucose value detection chips obtained in each of Embodiments and Comparative Embodiments. Incidentally, since the spacer thickness of the blood glucose value detection chip is 50 μm, the optical path length becomes 50 μm. For normalizing a difference in amount of the blood deposited between Embodiments and Comparative Embodiments, the absorbance (actual measurement value) in each measurement wavelength was corrected to the case of the clearance of 35 μm, and the transmittance was obtained from the corrected absorbance. A transmittance curve obtained from the spectrum analysis before the blood is deposited is shown in FIG. 7A. Incidentally, the correction of the absorbance was performed by dividing the absorbance (actual measurement value) in each measurement wavelength by the value of the clearance (CL) (μm) actually measured in each chip and further multiplying the obtained value by 35 (μm).

Figure 7B:
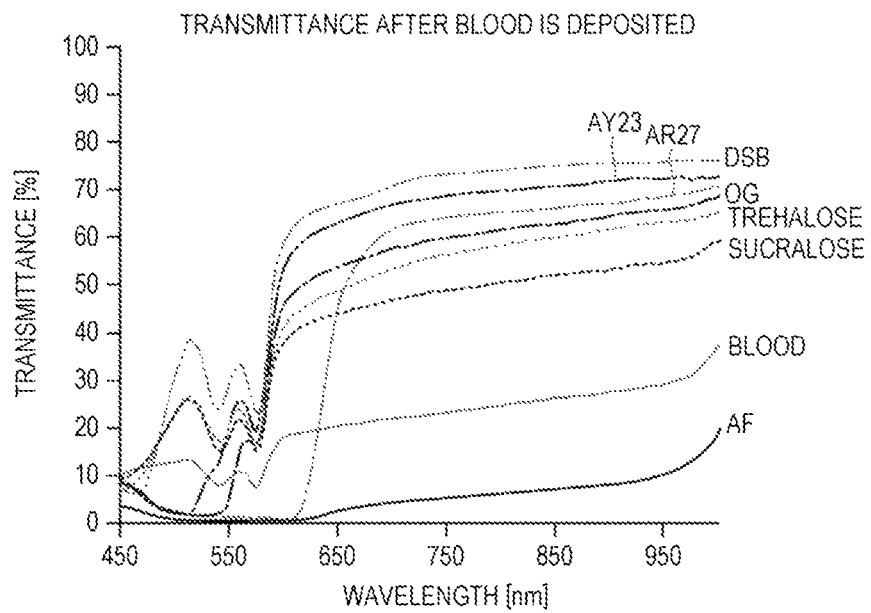
FIG. 7B shows transmittance curves (after blood is deposited) obtained by spectrum analysis of Embodiments, Comparative Embodiments, and Reference Embodiments (samples of blood).

Then, the blood sample (hematocrit value: 40) was deposited on the blood glucose value detection chip, and then the spectrum analysis at 10 to 15 seconds after the blood sample is deposited was performed. Based on the obtained spectrum analysis result, the absorbance was corrected similarly to the case before the blood sample is deposited and thus the transmittance was obtained. A transmittance curve obtained from the spectrum analysis after the blood is deposited is shown in FIG. 7B. Further, as an index indicating that the difference in refractive index between the red blood cell and the extra-red blood cell fluid is decreased, the transmittance at 810 nm is presented in Table 1.

From the transmittance curve after the blood sample is deposited, the transmittance of the peak minimal value observed in 545 nm and the transmittance of the peak minimal value observed at 575 nm were obtained. The results thereof are presented in Table 1. Incidentally, in Table 1, "⊙" represents that the transmittance of both the peak minimal values observed at 545 nm and 575 nm is 15% or more. In Table 1, "○" represents that the transmittance of any one of the peak minimal values observed at 545 nm and 575 nm is 15% or more. In Table 1, "X" represents that the peaks are not observed at 545 nm and 575 nm or the transmittance of both the peak minimal values observed at 545 nm and 575 nm is less than 15%. Incidentally, regarding Wst-1 in Comparative Embodiment 2 and Wst-8 in Comparative Embodiment 3, a value of the reduced body treated with a NaOH aqueous solution was described in Table 1.

In the conditions of respective Embodiments and Comparative Embodiments, the value of absorbance at 650 nm (the absorption peak wavelength of WST-4) measured using the chip before the blood sample is deposited is not substantially different from the absorbance value measured by dissolving the refractive index adjuster in water and setting an optical path length of 50 μm. Therefore, from the transmittance curve before the blood sample is deposited, the transmittance of the refractive index adjuster in 650 nm that is the absorption peak wavelength of WST-4 was obtained. The result thereof is presented in Table 1. Incidentally, in Table 1, "⊙" represents that the transmittance at 650 nm is 60% or more and 100% or less, "○" represents that the transmittance at 650 nm is 40% or more and less than 60%, and "X" represents that the transmittance at 650 nm is less than 40%.

<Precipitates>

In the production step of the blood glucose value detection chip, existence of precipitates was confirmed by visual inspection before drying after coating film formation.

<Degree of Solubility>

The degree of solubility of the refractive index adjuster presented in Table 1 is a degree of solubility with respect to water at 20° C. Incidentally, "X" in Table 1 means that the degree of solubility with respect to water at 20° C. is 50 mM or less.

Embodiment 1-1

A coating liquid was prepared by dissolving 35 μkat (2104 U) of glucose dehydrogenase (oxidoreductase; FAD-GDH GDL-351, TOYOBO CO., LTD.), 12.5 μmol of 2-benzothiazolyl-3-(4-carboxy-2-methoxyphenyl)-5-[4-(2-sulfoethyl-carbamoyl)phenyl]-2H-tetrazolium sodium salt (coloring reagent; WST-4, absorption peak wavelength 650 nm), 0.25 μmol of 1-methoxy-5-methylphenazinium methyl sulfate (electron carrier; m-PMS), and 22.5 μmol of Acid Yellow 23 (refractive index adjuster; AY23) in 162.5 μl of pure water.

[Chem. 7]

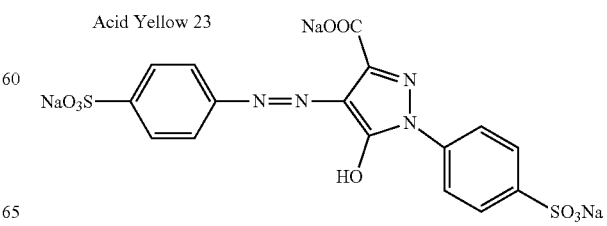

Acid Yellow 23

Figure 5A:
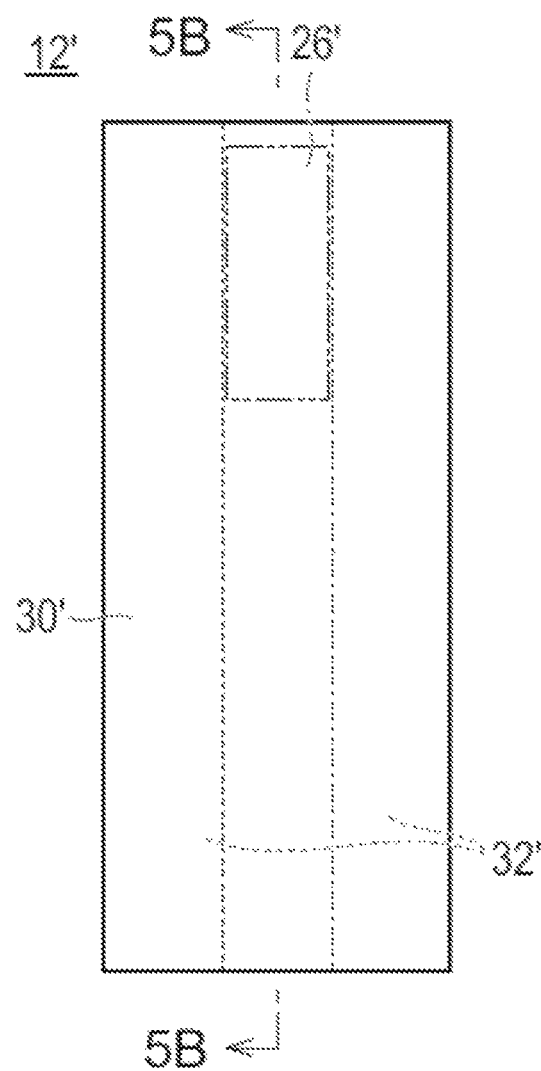
FIG. 5A is a diagram schematically illustrating a detection chip for an analyte used in Embodiments.
Figure 5B:
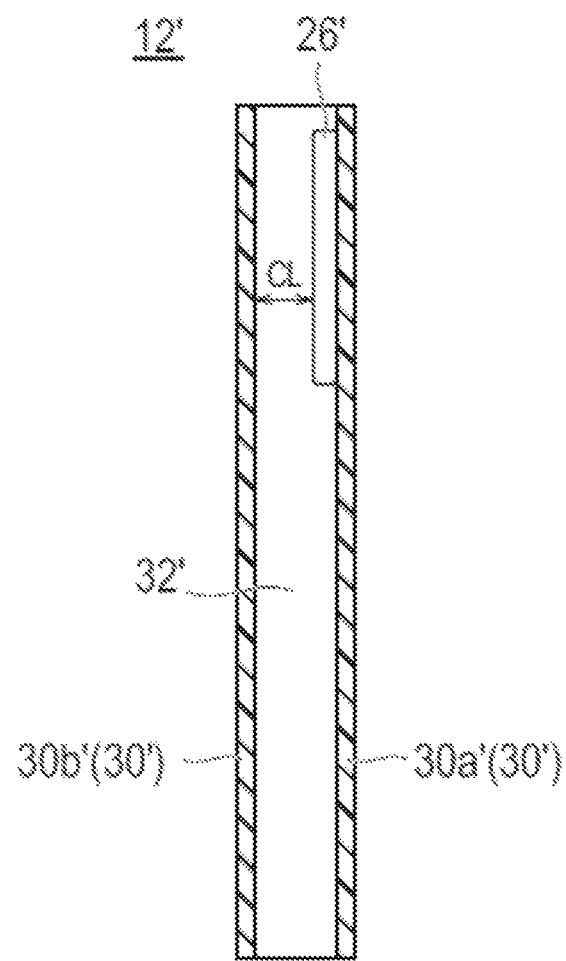
FIG. 5B is a diagram schematically illustrating a detection chip for an analyte used in Embodiments.

Next, the blood glucose value detection chip illustrated in FIG. 5 was prepared using the coating liquid. Specifically, the coating liquid was applied to a plate piece 30a' made of polyethylene terephthalate that had been subjected to a hydrophilization treatment such that the thickness thereof after drying had about 15 μm in a size of 1.5 mm×3 mm, and then the coating film was dried at 25° C. for 12 hours to form a reaction portion 26'. Subsequently, a pair of spacers 32' (polyester film base, thickness of 50 μm) was pasted to the plate piece 30a' by a pressure-sensitive adhesive in the right and left sides of the reaction portion 26' so as to be along both ends of the plate piece 30a'. Finally, a plate piece 30b' having the same size as that of the plate piece 30a' was pasted to a surface of the pair of spacers 32' opposite to the plate piece 30a' by a pressure-sensitive adhesive. In this way, a blood glucose value detection chip 12' was obtained. The thickness of the reaction portion 26' in the chip actually obtained was measured by Optical MicroGauge Thickness Gauge (C11011-01, Hamamatsu Photonics K.K.). The clearance (CL) between the plate piece 30b' and the reaction portion 26' was obtained by subtracting the thickness of the reaction portion 26' from the thickness (50 μm) of the spacer 32'.

Embodiment 1-2

A blood glucose value detection chip was obtained in the same manner as Embodiment 1-1, except that the amount of WST-4 in Embodiment 1-1 was changed to 49.9 μmol, and 27.1 μmol of 1,3-benzene disulfonate (DSB) was used instead of Acid Yellow 23.

Embodiment 1-3

A blood glucose value detection chip was obtained in the same manner as Embodiment 1-1, except that 30.2 μmol of sucralose was used instead of Acid Yellow 23 in Embodiment 1-1.

Embodiment 1-4

A blood glucose value detection chip was obtained in the same manner as Embodiment 1-1, except that 35.1 μmol of trehalose was used instead of Acid Yellow 23 in Embodiment 1-1.

Embodiment 1-5

A blood glucose value detection chip was obtained in the same manner as Embodiment 1-1, except that 26.5 μmol of Orange G (OG) was used instead of Acid Yellow 23 in Embodiment 1-1.

[Chem. 8]

Orange G

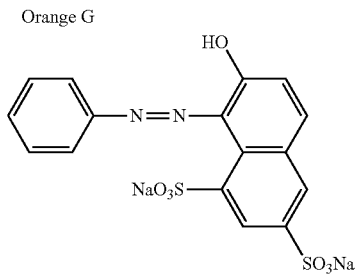

Embodiment 1-6

A blood glucose value detection chip was obtained in the same manner as Embodiment 1-1, except that 19.9 μmol of Acid Red 27 (AR27) was used instead of Acid Yellow 23 in Embodiment 1-1.

[Chem. 9]

Acid Red 27

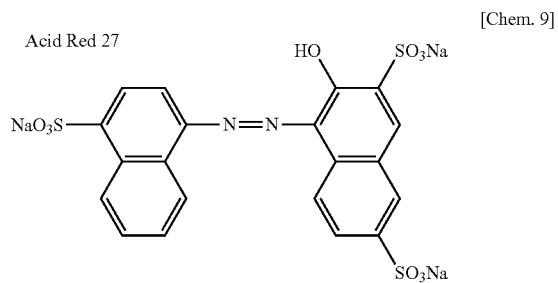

Comparative Embodiment 1

A blood glucose value detection chip was obtained in the same manner as Embodiment 1-1, except that 20.5 μmol of Acid Fuchsin (AF) was used instead of Acid Yellow 23 in Embodiment 1-1.

Comparative Embodiment 2

Although 18.4 μmol of 2-(4-iodophenyl)-3-(4-nitrophenyl)-5-(2,4-disulfophenyl)-2H-tetrazolium sodium salt was used instead of Acid Yellow 23 in Embodiment 1-1 in preparation of a coating liquid, solubility with respect to the blood sample was low, so that the spectrum analysis was not able to be performed.

Comparative Embodiment 3

Although 20.0 μmol of 2-(2-methoxy-4-nitrophenyl)-3-(4-nitrophenyl)-5-(2,4-disulfophenyl)-2H-tetrazolium sodium salt was used instead of Acid Yellow 23 in Embodiment 1-1 in preparation of a coating liquid, solubility with respect to the blood sample was low, so that the spectrum analysis was not able to be performed.

Comparative Embodiment 4

Although 22.0 μmol of Acid Blue 1 was used instead of Acid Yellow 23 in Embodiment 1-1 in preparation of a coating liquid, solubility with respect to water was low, and precipitates were generated from the coating liquid. Further, the solubility with respect to the blood sample was low, so that the spectrum analysis was not able to be performed.

Reference Embodiment 1

A chip was prepared in the same manner as Embodiment 1-1, except that the reaction portion 26' was not provided. The spectrum analysis of the blood sample was performed using the chip. Incidentally, the transmittance of blood (hematocrit value: 40) at a wavelength of 810 nm was 25%.

TABLE 1

| | Refractive index adjuster | | | Transmittance | | | | |
|---|---|---|---|---|---|---|---|---|
| | | Refractive index increasing capability | Red blood cell reducing capability (ΔHt) | 545 nm, 575 nm(Hb absorption peak wavelength) | 650 nm (Coloring reagent absorption peak wavelength) | 810 nm (Scattering light) | Precipitates | Degree of solubility |
| Embodiment 1-1 | Acid Yellow 23 | 0.000277 | 8.2 | ○ | ⊙ | 69.4% | Absent | 487 mM |
| Embodiment 1-2 | DSB | 0.000126 | 9.0 | ○ | ⊙ | 71.8% | Absent | 2.3 M |
| Embodiment 1-3 | Sucralose | 0.000129 | 0.5 | ○ | ⊙ | 51.8% | Absent | 820 mM |
| Embodiment 1-4 | Trehalose | 0.000109 | 3.5 | ○ | ⊙ | 58.3% | Absent | 200 mM |
| Embodiment 1-5 | Orange G | 0.000296 | 1.9 | ○ | ⊙ | 61.5% | Absent | 220 mM |
| Embodiment 1-6 | Acid Red 27 | 0.000381 | 6.7 | × | ○ | 65.6% | Absent | 83 mM |
| Comparative Embodiment 1 | Acid Fuchsin | 0.000259 | 14.3 | × | × | 6.2% | Absent | 340 mM |
| Comparative Embodiment 2 | Wst-1 | 0.000174 | Unmeasurable | ⊙ (Reduced body) | × | Not performed | Absent | × |
| Comparative Embodiment 3 | Wst-8 | 0.000189 | Unmeasurable | ⊙ (Reduced body) | × | Not performed | Absent | × |
| Comparative Embodiment 4 | Acid Blue 1 | Unmeasurable | Unmeasurable | × | × | Not performed | Present | × |

From the above Table 1 and FIG. 7B, in Embodiments, the transmittance in a long wavelength range is further improved than in the blood sample. From this point, it is known that the difference in refractive index between the red blood cell and the extra-red blood cell fluid is decreased so that scattering caused by the red blood cell that is noise is decreased. Thus, according to the present disclosure, an analyte can be detected with high accuracy without fractionation of a component derived from a blood sample.

Embodiment 2

A coating liquid was prepared by dissolving 35 μkat (2104 U) of glucose dehydrogenase (oxidoreductase; FAD-GDH GDL-351, TOYOBO CO., LTD.), 12.5 μmol of WST-4 (coloring reagent), 0.25 μmol of m-PMS (electron carrier), and 22.5 μmol of Acid Yellow 23 (refractive index adjuster; AY23) in 190 μl of pure water.

A blood glucose value detection chip was prepared by the same manner as Embodiment 1-1, except that the thickness of the coating film was changed as in the following Table 2. Incidentally, the thickness of the reaction portion 26' was adjusted by increasing the number of times of application. The thickness of the reaction portion 26' was measured by Optical MicroGauge Thickness Gauge (C11011-01, Hamamatsu Photonics K.K.). The clearance (CL) between the plate piece 30b' and the reaction portion 26' was obtained by subtracting the thickness of the reaction portion 26' from the thickness (50 μm) of the spacer 32'. The volume of the extra-red blood cell fluid after the blood is deposited and the concentration of each of the coloring reagent and the refractive index adjuster after the blood sample is deposited (concentration at the time of blood sample being deposited) were calculated by the following formula.

(Calculation of Volume after Blood Is Deposited)

Volume (L) of extra-red blood cell fluid after blood is deposited=Blood inflow amount (L)×(1−Hematocrit value×$10^{-2}$)=(Clearance (CL) (mm)× 1.5 (mm)×3 (mm)×$10^{-6}$)×0.6

(Coloring Reagent Concentration)

Coloring reagent concentration (mmol/L extra-red blood cell fluid)=Abundance (mmol) of coloring reagent/(Volume (L) of extra-red blood cell fluid after blood is deposited+Volume (L) of reaction portion 26')

(Refractive Index Adjuster Concentration)

Coloring reagent concentration (mmol/L extra-red blood cell fluid)=Abundance (mmol) of refractive index adjuster/(Volume (L) of extra-red blood cell fluid after blood is deposited+Volume (L) of reaction portion 26')

Figure 8:
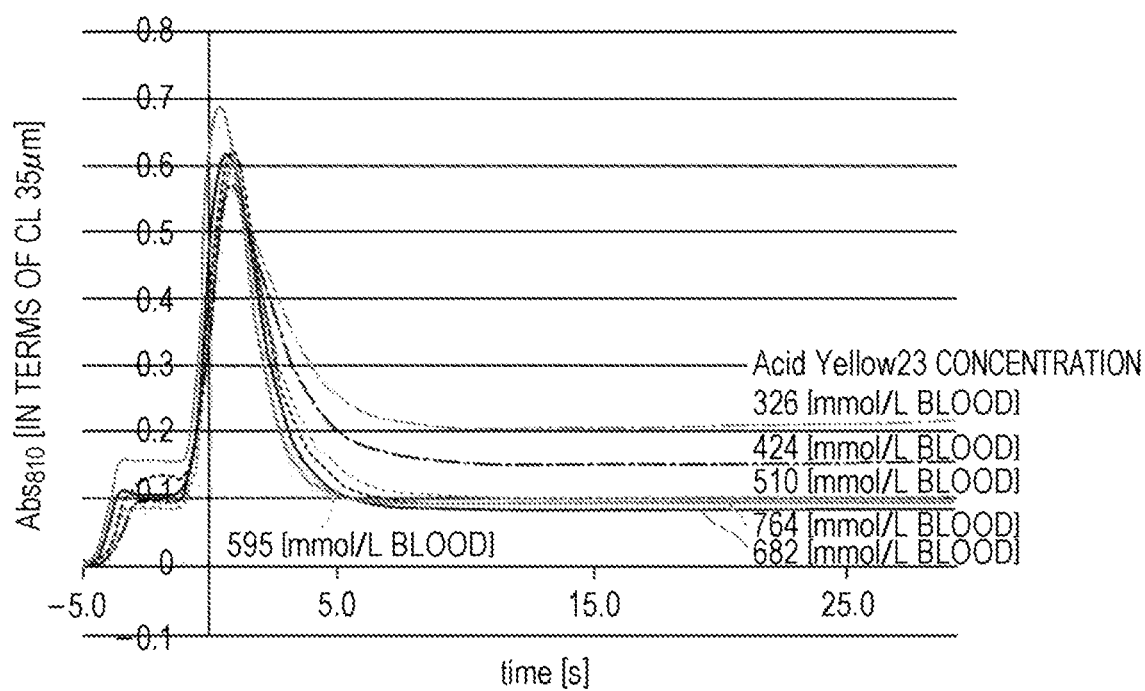
FIG. 8 shows a temporal change in absorbance of Embodiment 2 using Acid Yellow 23 as a refractive index adjuster, obtained by spectrum analysis.

The blood sample (hematocrit value: 40) was deposited on the blood glucose value detection chip, and then the absorbance (actual measurement value) in 810 nm was measured. For normalizing and comparing the amounts of the blood sample deposited between the respective blood glucose value detection chips, the clearance was corrected to 35 μm by dividing the absorbance (actual measurement value) by the value of clearance (μm) of each chip and further multiplying the obtained value by 35 (μm). The corrected absorbance Abs is shown in FIG. 8. Further, values (CL/$Abs_{810}$) obtained by dividing the clearance (actual measurement value) of each chip by the absorbance after 25 seconds from the blood sample being deposited (actual measurement value before correction with 35 μm) is presented in Table 2. CL/$Abs_{810}$ represents an influence rate of scattering light with respect to the clearance, and as this value is large, it is shown that occurrence of scattering light is efficiently suppressed.

TABLE 2

| Coating film thickness | Clearance (CL) | Concentration at the time of depositing [mmol/L extra-red blood cell fluid] | | |
|---|---|---|---|---|
| [μm] | [μm] | WST-4 | Acid Yellow 23 | CL/$Ab_{s810}$ |
| 7.7 | 42.3 | 181 | 326 | 164.5 |
| 9.7 | 40.3 | 236 | 424 | 224.9 |
| 13.0 | 37.0 | 284 | 510 | 340.3 |
| 15.5 | 34.5 | 331 | 595 | 415.7 |
| 17.2 | 32.8 | 379 | 682 | 408.2 |
| 19.1 | 30.9 | 425 | 764 | 365.0 |

Embodiment 3

Figure 9:
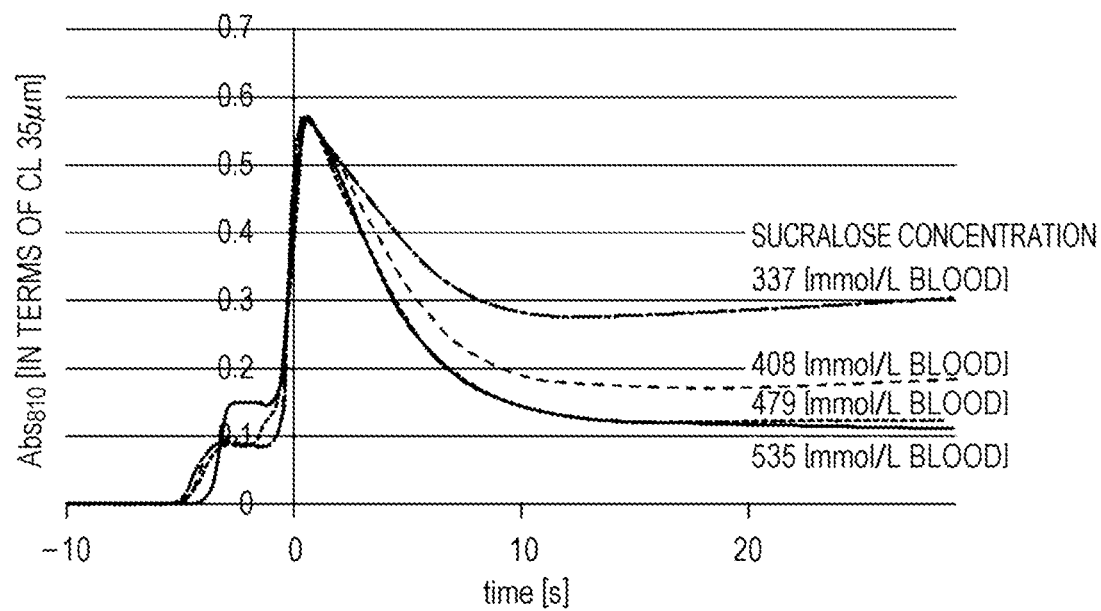
FIG. 9 shows a temporal change in absorbance of Embodiment 3 using sucralose as a refractive index adjuster, obtained by spectrum analysis.

A blood glucose value detection chip was prepared by the same manner as Embodiment 2, except that Acid Yellow 23 in Embodiment 2 was changed to sucralose. The results obtained by correcting the absorbance (actual measurement value) to the case of a clearance of 35 μm are shown in FIG. 9. Incidentally, the absorbance Abs of FIG. 9 was corrected by the same method as in Embodiment 2. Further, values ($CL/Abs_{810}$) obtained by dividing the clearance (actual measurement value) of each chip by the absorbance after 25 seconds from the blood sample being deposited (actual measurement value before correction with 35 μm) is presented in Table 3. $CL/Abs_{810}$ represents an influence rate of scattering light with respect to the clearance, and as this value is large, it is shown that occurrence of scattering light is efficiently suppressed.

TABLE 3

| Coating film thickness | Clearance (CL) | Concentration at the time of depositing [mmol/L extra-red blood cell fluid] | | $CL/Abs_{810}$ |
|---|---|---|---|---|
| [μm] | [μm] | WST-4 | Sucralose | |
| 7.5 | 42.5 | 224 | 337 | 119.0 |
| 9.9 | 40.1 | 273 | 408 | 196.6 |
| 11.9 | 38.1 | 319 | 479 | 295.7 |
| 15.8 | 34.2 | 356 | 535 | 323.7 |

REFERENCE SIGNS LIST

10 DETECTION APPARATUS
12, 12' DETECTION CHIP
14 MEASUREMENT UNIT
16 APPARATUS MAIN BODY
18 CHIP MAIN BODY PORTION
20 CAVITY
20a DISTAL END PORT
20b PROXIMAL END PORT
22 LONG SIDE
22a UPPER LONG SIDE
22b LOWER LONG SIDE
24 SHORT SIDE
24a DISTAL END SIDE
24b PROXIMAL END SIDE
26, 26' REACTION PORTION
28 MEASUREMENT TARGET PORTION
30, 30' PLATE PIECE
32, 32' SPACER
40 HOUSING
42 CONTROL UNIT
44 BOX PORTION
46 PHOTOMETRIC BLOCK
48 POWER BUTTON
50 OPERATION BUTTON
52 DISPLAY
54 EJECT LEVER
56 EJECT PIN
56a STICK PORTION
56b RECEIVING PORTION
58 INSERTION PORT
58a INSERTION OPENING PORTION
59 MEASUREMENT HOLE PORTION
60 CHIP MOUNTING PORTION
60a FLANGE PORTION
62 WALL PORTION
64 ELEMENT STORAGE SPACE
66 LIGHT GUIDE PORTION
68 LIGHT EMITTING ELEMENT
70 LIGHT EMITTING PORTION
72 LIGHT RECEIVING ELEMENT
74 LIGHT RECEIVING PORTION
76 COIL SPRING

The invention claimed is:

1. A composition for detecting an analyte in a blood sample, the composition comprising:
a coloring reagent that causes a chromogenic reaction upon dissolving in blood;
an oxidoreductase; and
a refractive index adjuster;
wherein the refractive index adjuster comprises a compound represented by Formula (1) below or a salt thereof:

$$Q^1\text{—}N\text{=}N\text{—}Q^2 \qquad \text{Formula (1)}$$

where each of $Q^1$ and $Q^2$ represents an aryl group or a nitrogen-containing heterocyclic group, which may have one or more substituents selected from the group consisting of: a halogen atom, a hydroxy group, an alkyl group having 1 to 3 carbon atoms, an alkoxy group having 1 to 3 carbon atoms, a carboxy group, a sulfo group, an amino group, a carbamoyl group, a sulfamoyl group, a phenyl group, a carboxyphenyl group, and a sulfophenyl group.

2. The composition according to claim 1, wherein:
a molar absorbance coefficient of the refractive index adjuster at an absorption peak wavelength of the coloring reagent is 200 L/(mol·cm) or less.

3. The composition according to claim 1, wherein the coloring reagent is a tetrazolium salt.

4. The composition according to claim 1, wherein:
the refractive index adjuster further comprises a benzenesulfonic acid compound or a salt thereof.

5. The composition according to claim 1, wherein:
the refractive index adjuster further comprises a disaccharide or a salt thereof.

6. The composition according to claim 1, wherein a content of the refractive index adjuster is 0.2 to 5 mol with respect to 1 mol of the coloring reagent.

7. The composition according to claim 1, wherein the analyte is selected from the group consisting of glucose, cholesterol, neutral fat, nicotinamide adenine dinucleotide phosphate, nicotinamide adenine dinucleotide, and uric acid.

8. A chip for detecting an analyte in a blood sample, the chip comprising:
a reaction portion containing a coloring reagent that causes a chromogenic reaction upon dissolving in blood, an oxidoreductase, and a refractive index adjuster;
wherein the refractive index adjuster comprises a compound represented by Formula (1) below or a salt thereof:

$$Q^1\text{-}N\text{=}N\text{-}Q^2 \qquad \text{Formula (1)}$$

where each of $Q^1$ and $Q^2$ represents an aryl group or a nitrogen-containing heterocyclic group, which may have one or more substituents selected from the group consisting of: a halogen atom, a hydroxy group, an alkyl group having 1 to 3 carbon atoms, an alkoxy group having 1 to 3 carbon atoms, a carboxy group, a sulfo group, an amino group, a carbamoyl group, a sulfamoyl group, a phenyl group, a carboxyphenyl group, and a sulfophenyl group.

* * * * *